(12) United States Patent
Warner et al.

(10) Patent No.: US 8,710,279 B2
(45) Date of Patent: Apr. 29, 2014

(54) HYDROGENOLYSIS OF ETHYL ACETATE IN ALCOHOL SEPARATION PROCESSES

(75) Inventors: R. Jay Warner, Houston, TX (US); Trinity Horton, Houston, TX (US); Radmila Jevtic, Pasadena, TX (US); Victor J. Johnston, Houston, TX (US); David Lee, Seabrook, TX (US); Adam Orosco, Houston, TX (US); Lincoln Sarager, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 304 days.

(21) Appl. No.: 13/094,714

(22) Filed: Apr. 26, 2011

(65) Prior Publication Data

US 2012/0010446 A1  Jan. 12, 2012

Related U.S. Application Data

(60) Provisional application No. 61/363,056, filed on Jul. 9, 2010.

(51) Int. Cl.
    C07C 27/04 (2006.01)

(52) U.S. Cl.
    USPC .......................................... 568/884; 568/885

(58) Field of Classification Search
    USPC ................................................. 568/884, 885
    See application file for complete search history.

(56) References Cited

U.S. PATENT DOCUMENTS

| | | |
|---|---|---|
| 1,939,116 A | 12/1933 | Fuchs |
| 2,607,807 A | 8/1952 | Ford |
| 2,649,407 A | 8/1953 | Harrison et al. |
| 2,702,783 A | 2/1955 | Harrison et al. |
| 2,801,209 A | 7/1957 | Muller et al. |
| 2,882,244 A | 4/1959 | Milton |
| 3,102,150 A | 8/1963 | Hunter et al. |
| 3,130,007 A | 4/1964 | Breck |
| 3,408,267 A | 10/1968 | Miller |
| 3,445,345 A | 5/1969 | Adam |
| 3,478,112 A | 11/1969 | Adam |
| 3,709,795 A | 1/1973 | Singleton |
| 3,769,329 A | 10/1973 | Knox et al. |
| 3,864,284 A | 2/1975 | Clippinger et al. |
| 3,884,981 A | 5/1975 | Kiff |
| 3,925,490 A | 12/1975 | Reich et al. |
| 3,990,952 A | 11/1976 | Katzen |
| 4,008,131 A | 2/1977 | Price |
| 4,039,395 A | 8/1977 | Eby |
| 4,107,002 A | 8/1978 | Eck et al. |
| 4,126,539 A | 11/1978 | Derr, Jr. et al. |
| 4,149,940 A | 4/1979 | Pinto |
| 4,262,154 A | 4/1981 | Gane et al. |
| 4,275,228 A | 6/1981 | Gruffaz |
| 4,306,942 A | 12/1981 | Brush |
| 4,317,918 A | 3/1982 | Takano et al. |
| 4,319,058 A | 3/1982 | Kulprathipanja |
| 4,328,375 A | 5/1982 | Barlow |
| 4,338,221 A | 7/1982 | Qualeatti |
| 4,352,940 A | 10/1982 | Adelman |
| 4,352,947 A | 10/1982 | Habib et al. |
| 4,370,491 A | 1/1983 | Bott et al. |
| 4,379,028 A | 4/1983 | Berg et al. |
| 4,395,576 A | 7/1983 | Kwantes et al. |
| 4,398,039 A | 8/1983 | Pesa |
| 4,409,405 A | 10/1983 | Lin et al. |
| 4,421,939 A | 12/1983 | Kiff et al. |
| 4,422,903 A | 12/1983 | Messick et al. |
| 4,429,056 A | 1/1984 | Smith |
| 4,430,506 A | 2/1984 | Gauthier-Lafaye et al. |
| 4,443,639 A | 4/1984 | Pesa et al. |
| 4,451,677 A | 5/1984 | Bradley et al. |
| 4,454,358 A | 6/1984 | Kummer |
| 4,456,775 A | 6/1984 | Travers |
| 4,465,854 A | 8/1984 | Pond |
| 4,471,136 A | 9/1984 | Larkins |
| 4,476,326 A | 10/1984 | Lin et al. |
| 4,480,115 A | 10/1984 | McGinnis |
| 4,481,146 A | 11/1984 | Leupold et al. |
| 4,492,808 A | 1/1985 | Hagen |
| 4,497,967 A | 2/1985 | Wan |
| 4,514,515 A | 4/1985 | Travers et al. |
| 4,514,521 A | 4/1985 | Smith |
| 4,517,391 A | 5/1985 | Schuster et al. |
| 4,520,213 A | 5/1985 | Victor |
| 4,541,897 A | 9/1985 | Sommer et al. |

(Continued)

FOREIGN PATENT DOCUMENTS

| | | |
|---|---|---|
| CA | 1233484 | 3/1988 |
| CN | 1230458 | 10/1999 |

(Continued)

OTHER PUBLICATIONS

International Search Report and Written Opinion mailed Sep. 2, 2011 in corresponding International Application No. PCT/US2011/023276.

(Continued)

*Primary Examiner* — Sikarl Witherspoon

(57) ABSTRACT

Recovery of ethanol from a crude ethanol product obtained from the hydrogenation of acetic acid and by reacting a portion of the crude ethanol product or one or more derivative streams containing ethyl acetate obtained therefrom in the presence of hydrogen, via hydrogenolysis. The one or more derivative streams comprise ethyl acetate that are reacted in via hydrogenolysis form additional ethanol that may be directly or indirectly fed to the separation zone or the hydrogenation reactor.

36 Claims, 7 Drawing Sheets

(56) References Cited

U.S. PATENT DOCUMENTS

| | | |
|---|---|---|
| 4,556,644 A | 12/1985 | Erpenbach et al. |
| 4,569,726 A | 2/1986 | Berg et al. |
| 4,611,085 A | 9/1986 | Kitson |
| 4,626,321 A | 12/1986 | Grethlein |
| 4,626,604 A | 12/1986 | Hiles et al. |
| 4,628,130 A | 12/1986 | Bournonville |
| 4,629,711 A | 12/1986 | Erpenbach et al. |
| 4,664,753 A | 5/1987 | Erpenbach et al. |
| 4,678,543 A | 7/1987 | Houben |
| 4,692,218 A | 9/1987 | Houben |
| 4,737,318 A | 4/1988 | Ichino et al. |
| 4,751,334 A | 6/1988 | Turner et al. |
| 4,758,600 A | 7/1988 | Arimitsu et al. |
| 4,762,817 A | 8/1988 | Logsdon et al. |
| 4,777,303 A | 10/1988 | Kitson et al. |
| 4,804,791 A | 2/1989 | Kitson et al. |
| 4,826,795 A | 5/1989 | Kitson et al. |
| 4,837,367 A | 6/1989 | Gustafson et al. |
| 4,837,368 A | 6/1989 | Gustafson et al. |
| 4,842,693 A | 6/1989 | Wheldon |
| 4,876,402 A | 10/1989 | Logsdon et al. |
| 4,886,905 A | 12/1989 | Larkins, Jr. |
| 4,908,477 A | 3/1990 | Hartmann et al. |
| 4,961,826 A | 10/1990 | Grethlein |
| 4,978,778 A | 12/1990 | Isshiki et al. |
| 4,985,572 A | 1/1991 | Kitson |
| 4,990,655 A | 2/1991 | Kitson |
| 4,992,582 A | 2/1991 | Ruppert et al. |
| 4,994,608 A | 2/1991 | Torrence |
| 5,001,259 A | 3/1991 | Smith |
| 5,004,845 A | 4/1991 | Bradley et al. |
| 5,026,908 A | 6/1991 | Smith |
| 5,035,776 A | 7/1991 | Knapp |
| 5,047,592 A | 9/1991 | Carpenter |
| 5,061,671 A | 10/1991 | Kitson et al. |
| 5,070,016 A | 12/1991 | Hallberg |
| 5,124,004 A | 6/1992 | Grethlein |
| 5,144,068 A | 9/1992 | Smith |
| 5,149,680 A | 9/1992 | Kitson |
| 5,185,476 A | 2/1993 | Gustafson |
| 5,185,481 A | 2/1993 | Muto |
| 5,196,601 A | 3/1993 | Kitsuki et al. |
| 5,198,592 A | 3/1993 | van Beijnum |
| 5,215,902 A | 6/1993 | Tedder |
| 5,220,020 A | 6/1993 | Buchwald et al. |
| 5,227,141 A | 7/1993 | Kim et al. |
| 5,233,099 A | 8/1993 | Tabata et al. |
| 5,237,108 A | 8/1993 | Marraccini et al. |
| 5,241,106 A | 8/1993 | Inoue et al. |
| 5,243,095 A | 9/1993 | Roberts et al. |
| 5,250,271 A | 10/1993 | Horizoe |
| 5,254,758 A | 10/1993 | Hiles et al. |
| 5,300,685 A | 4/1994 | Scates et al. |
| 5,334,751 A | 8/1994 | Lemanski et al. |
| 5,348,625 A | 9/1994 | Berg |
| 5,362,918 A | 11/1994 | Aizawa et al. |
| 5,399,752 A | 3/1995 | Okrasinski et al. |
| 5,403,962 A | 4/1995 | Schneider et al. |
| 5,414,161 A | 5/1995 | Uhm |
| 5,415,741 A | 5/1995 | Berg |
| 5,416,237 A | 5/1995 | Aubigne et al. |
| 5,426,246 A | 6/1995 | Nagahara |
| 5,437,770 A | 8/1995 | Berg |
| 5,445,716 A | 8/1995 | Berg |
| 5,449,440 A | 9/1995 | Rescalli et al. |
| 5,476,974 A | 12/1995 | Moore et al. |
| 5,480,665 A | 1/1996 | Smith |
| 5,502,094 A | 3/1996 | Moore et al. |
| 5,502,248 A | 3/1996 | Funk |
| 5,527,969 A | 6/1996 | Kaufhold et al. |
| 5,567,765 A | 10/1996 | Moore et al. |
| RE35,377 E | 11/1996 | Steinberg |
| 5,599,976 A | 2/1997 | Scates |
| 5,658,962 A | 8/1997 | Moore et al. |
| 5,696,284 A | 12/1997 | Baker et al. |
| 5,731,252 A | 3/1998 | Warner et al. |
| 5,747,486 A | 5/1998 | Sohda et al. |
| 5,762,765 A | 6/1998 | Berg |
| 5,770,761 A | 6/1998 | Lin et al. |
| 5,770,770 A | 6/1998 | Kim |
| 5,800,681 A | 9/1998 | Berg |
| 5,821,111 A | 10/1998 | Grady |
| 5,831,133 A | 11/1998 | Mimoun |
| 5,861,530 A | 1/1999 | Atkins |
| 5,877,347 A | 3/1999 | Ditzel et al. |
| 5,877,348 A | 3/1999 | Ditzel et al. |
| 5,883,295 A | 3/1999 | Sunley et al. |
| 5,932,764 A | 8/1999 | Morris et al. |
| 5,942,460 A | 8/1999 | Garland et al. |
| 5,973,193 A | 10/1999 | Crane |
| 5,993,610 A | 11/1999 | Berg |
| 5,998,658 A | 12/1999 | Wu et al. |
| 6,024,176 A | 2/2000 | Moore et al. |
| 6,040,474 A | 3/2000 | Jobson |
| 6,046,127 A | 4/2000 | Mimoun |
| 6,093,845 A | 7/2000 | van Acker |
| 6,121,497 A | 9/2000 | Murphy |
| 6,121,498 A | 9/2000 | Tustin et al. |
| 6,140,535 A | 10/2000 | Williams |
| 6,143,930 A | 11/2000 | Singh |
| 6,204,299 B1 | 3/2001 | Moore et al. |
| 6,214,253 B1 | 4/2001 | Moore et al. |
| 6,232,352 B1 | 5/2001 | Vidalin |
| 6,294,703 B1 | 9/2001 | Hara et al. |
| 6,326,515 B1 | 12/2001 | Clode et al. |
| 6,361,713 B1 | 3/2002 | Moore et al. |
| 6,375,807 B1 | 4/2002 | Nieuwoudt et al. |
| 6,403,840 B1 | 6/2002 | Zhou et al. |
| 6,458,996 B1 | 10/2002 | Muskett |
| 6,462,231 B1 | 10/2002 | Yanagawa et al. |
| 6,462,243 B1 | 10/2002 | Zhou et al. |
| 6,465,696 B1 | 10/2002 | Zhou et al. |
| 6,465,699 B1 | 10/2002 | Grosso |
| 6,472,555 B2 | 10/2002 | Choudary |
| 6,472,572 B1 | 10/2002 | Zhou et al. |
| 6,486,366 B1 | 11/2002 | Ostgard et al. |
| 6,486,368 B1 | 11/2002 | Zhou et al. |
| 6,491,983 B2 | 12/2002 | Moore et al. |
| 6,495,730 B1 | 12/2002 | Konishi et al. |
| 6,509,180 B1 | 1/2003 | Verser |
| 6,509,290 B1 | 1/2003 | Vaughn et al. |
| 6,525,230 B2 | 2/2003 | Grosso |
| 6,552,220 B1 | 4/2003 | Obana et al. |
| 6,627,770 B1 | 9/2003 | Cheung |
| 6,632,330 B1 | 10/2003 | Colley |
| 6,657,078 B2 | 12/2003 | Scates |
| 6,670,490 B1 | 12/2003 | Campos et al. |
| 6,685,754 B2 | 2/2004 | Kindig |
| 6,693,213 B1 | 2/2004 | Kolena |
| 6,696,596 B1 | 2/2004 | Herzog et al. |
| 6,713,655 B2 | 3/2004 | Yilmaz et al. |
| 6,723,886 B2 | 4/2004 | Allison |
| 6,755,975 B2 | 6/2004 | Vane et al. |
| 6,765,110 B2 | 7/2004 | Warner |
| 6,768,021 B2 | 7/2004 | Horan |
| 6,809,217 B1 | 10/2004 | Colley et al. |
| 6,863,211 B2 | 3/2005 | Moore et al. |
| 6,867,164 B2 | 3/2005 | Obana et al. |
| 6,903,045 B2 | 6/2005 | Zoeller et al. |
| 6,906,228 B2 | 6/2005 | Fischer |
| 6,927,048 B2 | 8/2005 | Verser |
| 7,005,541 B2 | 2/2006 | Cheung |
| 7,019,182 B2 | 3/2006 | Grosso |
| 7,074,603 B2 | 7/2006 | Verser |
| 7,084,312 B1 | 8/2006 | Huber et al. |
| 7,091,155 B2 | 8/2006 | Inui et al. |
| 7,115,772 B2 | 10/2006 | Picard |
| 7,148,390 B2 | 12/2006 | Inui et al. |
| 7,161,050 B2 | 1/2007 | Sherman et al. |
| 7,208,624 B2 | 4/2007 | Scates |
| 7,223,886 B2 | 5/2007 | Scates et al. |
| 7,230,150 B2 | 6/2007 | Grosso et al. |
| 7,297,236 B1 | 11/2007 | Vander Griend |
| 7,351,559 B2 | 4/2008 | Verser |

(56) References Cited

U.S. PATENT DOCUMENTS

| | | |
|---|---|---|
| 7,361,794 B2 | 4/2008 | Grosso |
| 7,375,049 B2 | 5/2008 | Hayes et al. |
| 7,399,892 B2 | 7/2008 | Rix et al. |
| 7,507,562 B2 | 3/2009 | Verser |
| 7,538,060 B2 | 5/2009 | Barnicki et al. |
| 7,553,397 B1 | 6/2009 | Colley |
| 7,572,353 B1 | 8/2009 | Vander Griend |
| 7,601,865 B2 | 10/2009 | Verser |
| 7,608,744 B1 | 10/2009 | Johnston |
| 7,652,167 B2 | 1/2010 | Miller et al. |
| 7,667,068 B2 | 2/2010 | Miller et al. |
| 7,678,940 B2 | 3/2010 | Miura et al. |
| 7,682,812 B2 | 3/2010 | Verser |
| 7,700,814 B2 | 4/2010 | Garton et al. |
| 7,732,173 B2 | 6/2010 | Mairal et al. |
| 7,744,727 B2 | 6/2010 | Blum et al. |
| 7,820,852 B2 | 10/2010 | Johnston et al. |
| 7,834,223 B2 | 11/2010 | Atkins et al. |
| 7,838,708 B2 | 11/2010 | Sherman et al. |
| 7,842,844 B2 | 11/2010 | Atkins |
| 7,863,489 B2 | 1/2011 | Johnston |
| 7,884,253 B2 | 2/2011 | Stites |
| 7,888,082 B2 | 2/2011 | Verser |
| 7,906,680 B2 | 3/2011 | Scates et al. |
| 7,947,746 B2 | 5/2011 | Scates et al. |
| 7,964,379 B2 | 6/2011 | Verser et al. |
| 7,994,368 B2 | 8/2011 | Johnston et al. |
| 8,071,821 B2 | 12/2011 | Johnston et al. |
| 2001/0027172 A1 | 10/2001 | Moore et al. |
| 2002/0156328 A1 | 10/2002 | Grosso |
| 2002/0198416 A1 | 12/2002 | Zhou et al. |
| 2003/0013908 A1 | 1/2003 | Horan |
| 2003/0069452 A1 | 4/2003 | Sherman et al. |
| 2003/0077771 A1 | 4/2003 | Verser et al. |
| 2003/0078456 A1 | 4/2003 | Yilmaz et al. |
| 2003/0104587 A1 | 6/2003 | Verser et al. |
| 2003/0114719 A1 | 6/2003 | Fischer et al. |
| 2003/0120121 A1 | 6/2003 | Sherman et al. |
| 2003/0125585 A1 | 7/2003 | Yilmaz et al. |
| 2003/0125589 A1 | 7/2003 | Grosso |
| 2003/0135069 A1 | 7/2003 | Fujita et al. |
| 2003/0153059 A1 | 8/2003 | Pilkington et al. |
| 2003/0166973 A1 | 9/2003 | Zhou et al. |
| 2004/0006246 A1 | 1/2004 | Sherman et al. |
| 2004/0009614 A1 | 1/2004 | Ahn et al. |
| 2004/0063184 A1 | 4/2004 | Grichko |
| 2004/0152915 A1 | 8/2004 | Fujita et al. |
| 2004/0232049 A1 | 11/2004 | Dath et al. |
| 2004/0242917 A1 | 12/2004 | Inui et al. |
| 2004/0267074 A1 | 12/2004 | Grosso et al. |
| 2005/0043572 A1 | 2/2005 | Grosso |
| 2005/0192468 A1 | 9/2005 | Sherman et al. |
| 2005/0209328 A1 | 9/2005 | Allgood et al. |
| 2005/0214408 A1 | 9/2005 | Pilkington et al. |
| 2006/0019360 A1 | 1/2006 | Verser |
| 2006/0106246 A1 | 5/2006 | Warner |
| 2006/0127999 A1 | 6/2006 | Verser |
| 2006/0224013 A1 | 10/2006 | Inui et al. |
| 2006/0247466 A1 | 11/2006 | Zinobile et al. |
| 2006/0252956 A1 | 11/2006 | Miller et al. |
| 2007/0031954 A1 | 2/2007 | Mairal et al. |
| 2007/0265360 A1 | 11/2007 | Luo et al. |
| 2007/0270511 A1 | 11/2007 | Melnichuk |
| 2008/0103335 A1 | 5/2008 | Scates et al. |
| 2008/0135396 A1 | 6/2008 | Blum |
| 2008/0187472 A1 | 8/2008 | Ahn et al. |
| 2008/0193989 A1 | 8/2008 | Verser |
| 2008/0207953 A1 | 8/2008 | Houssin et al. |
| 2008/0257784 A1 | 10/2008 | Dath et al. |
| 2008/0269518 A1 | 10/2008 | Scates et al. |
| 2009/0005588 A1 | 1/2009 | Hassan |
| 2009/0014313 A1 | 1/2009 | Lee et al. |
| 2009/0023192 A1 | 1/2009 | Verser |
| 2009/0069609 A1 | 3/2009 | Kharas |
| 2009/0081749 A1 | 3/2009 | Verser et al. |
| 2009/0099389 A1 | 4/2009 | Shaver |
| 2009/0166172 A1 | 7/2009 | Casey et al. |
| 2009/0221725 A1 | 9/2009 | Chornet et al. |
| 2009/0264285 A1 | 10/2009 | Luo et al. |
| 2009/0270651 A1 | 10/2009 | Zinobile et al. |
| 2009/0281354 A1 | 11/2009 | Mariansky |
| 2009/0299092 A1 | 12/2009 | Beavis et al. |
| 2009/0318573 A1 | 12/2009 | Stites et al. |
| 2009/0326080 A1 | 12/2009 | Chornet et al. |
| 2009/0326268 A1 | 12/2009 | Hanes et al. |
| 2010/0016454 A1 | 1/2010 | Gracey et al. |
| 2010/0029980 A1 | 2/2010 | Johnston |
| 2010/0029993 A1 | 2/2010 | Johnston et al. |
| 2010/0029995 A1 | 2/2010 | Johnston |
| 2010/0029996 A1 | 2/2010 | Danjo et al. |
| 2010/0030001 A1 | 2/2010 | Chen |
| 2010/0030002 A1 | 2/2010 | Johnston |
| 2010/0041919 A1 | 2/2010 | Wu et al. |
| 2010/0063319 A1 | 3/2010 | Brtko et al. |
| 2010/0069515 A1 | 3/2010 | Tirtowidjojo et al. |
| 2010/0080736 A1 | 4/2010 | Hassan et al. |
| 2010/0121114 A1 | 5/2010 | Weiner |
| 2010/0121119 A1 | 5/2010 | Sherman et al. |
| 2010/0137630 A1 | 6/2010 | Garton et al. |
| 2010/0145097 A1 | 6/2010 | Brtko et al. |
| 2010/0185021 A1 | 7/2010 | Ross et al. |
| 2010/0196789 A1 | 8/2010 | Fisher et al. |
| 2010/0197485 A1 | 8/2010 | Johnston |
| 2010/0197959 A1 | 8/2010 | Johnston |
| 2010/0197985 A1 | 8/2010 | Johnston et al. |
| 2010/0204512 A1 | 8/2010 | Kimmich et al. |
| 2010/0249479 A1 | 9/2010 | Berg-Slot et al. |
| 2010/0261800 A1 | 10/2010 | Daniel et al. |
| 2010/0273229 A1 | 10/2010 | Verser |
| 2010/0311138 A1 | 12/2010 | Padgett |
| 2011/0004033 A1 | 1/2011 | Johnston et al. |
| 2011/0004034 A1 | 1/2011 | Daniel et al. |
| 2011/0034741 A1 | 2/2011 | Sherman et al. |
| 2011/0046421 A1 | 2/2011 | Daniel |
| 2011/0082322 A1 | 4/2011 | Jevtic et al. |
| 2011/0098501 A1 | 4/2011 | Johnston |
| 2011/0190547 A1 | 8/2011 | Jevtic et al. |
| 2011/0190548 A1 | 8/2011 | Jevtic et al. |
| 2011/0190552 A1 | 8/2011 | Powell et al. |
| 2011/0224462 A1 | 9/2011 | Ditzel et al. |
| 2011/0263911 A1 | 10/2011 | Johnston et al. |
| 2011/0275861 A1 | 11/2011 | Johnston |
| 2011/0275862 A1 | 11/2011 | Johnston et al. |
| 2012/0010438 A1 | 1/2012 | Lee et al. |
| 2012/0010445 A1 | 1/2012 | Johnston et al. |

FOREIGN PATENT DOCUMENTS

| | | |
|---|---|---|
| CN | 1944373 | 4/2007 |
| CN | 1944374 | 4/2007 |
| CN | 101665424 | 3/2010 |
| CN | 201768393 | 3/2011 |
| CN | 102228831 | 11/2011 |
| CN | 102229520 | 11/2011 |
| DE | 241590 | 12/1986 |
| DE | 60025239 | 6/2006 |
| EP | 0056488 | 7/1982 |
| EP | 0104197 | 4/1984 |
| EP | 0137749 | 4/1985 |
| EP | 0167300 | 1/1986 |
| EP | 0175558 | 3/1986 |
| EP | 0192587 | 8/1986 |
| EP | 0198682 | 10/1986 |
| EP | 0285420 | 10/1988 |
| EP | 0285786 | 10/1988 |
| EP | 0372847 | 6/1990 |
| EP | 0456647 | 7/1990 |
| EP | 0400904 | 12/1990 |
| EP | 0535825 | 5/1996 |
| EP | 0944572 | 9/1999 |
| EP | 0990638 | 4/2000 |
| EP | 0992482 | 4/2000 |
| EP | 1338587 | 8/2003 |
| EP | 2060553 | 5/2009 |

(56) References Cited

FOREIGN PATENT DOCUMENTS

| EP | 2060555 | 5/2009 |
|---|---|---|
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| JP | 60-09454 | 1/1985 |
| JP | 60-25033 | 2/1985 |
| JP | 61-28181 | 2/1986 |
| JP | 02-215790 | 8/1990 |
| JP | 4-193304 | 7/1992 |
| JP | 51-86391 | 7/1993 |
| JP | 6-116182 | 4/1994 |
| JP | 2001-046874 | 2/2001 |
| JP | 2001-157841 | 6/2001 |
| JP | 2005-289936 | 10/2005 |
| KR | 2012 0010763 | 2/2012 |
| WO | WO 82/03854 | 11/1982 |
| WO | 8303409 | 10/1983 |
| WO | WO 98/25876 | 6/1998 |
| WO | WO 02/092541 | 11/2002 |
| WO | WO 2005/102513 | 11/2005 |
| WO | WO 2007/003897 | 1/2007 |
| WO | WO 2008/135192 | 11/2008 |
| WO | 2009009320 | 1/2009 |
| WO | WO 2009/009322 | 1/2009 |
| WO | WO 2009/009323 | 1/2009 |
| WO | WO 2009/048335 | 4/2009 |
| WO | 2009063174 | 5/2009 |
| WO | 2009063176 | 5/2009 |
| WO | WO 2009/077719 | 6/2009 |
| WO | WO 2009/077720 | 6/2009 |
| WO | WO 2009/077725 | 6/2009 |
| WO | WO 2009/077729 | 6/2009 |
| WO | WO 2009/103948 | 8/2009 |
| WO | 2009105860 | 9/2009 |
| WO | WO 2010/014145 | 2/2010 |
| WO | WO 2010/014151 | 2/2010 |
| WO | WO 2010/014153 | 2/2010 |
| WO | WO 2010/030320 | 3/2010 |
| WO | 2010055285 | 5/2010 |
| WO | WO 2011/053365 | 5/2011 |
| WO | WO 2011/056597 | 5/2011 |
| WO | WO 2011/097208 | 8/2011 |

OTHER PUBLICATIONS

Written Opinion mailed May 8, 2012 in corresponding International Application No. PCT/US2011/023276.
International Preliminary Report on Patentability mailed Jun. 27, 2012 in corresponding International Application No. PCT/US2011/023276.
International Search Report and Written Opinion mailed on Aug. 11, 2011 in corresponding International Application No. PCT/US2011/023283.
Written Opinion mailed on Jan. 30, 2012 in corresponding International Application No. PCT/US2011/023283.
International Search Report and Written Opinion mailed Sep. 6, 2011 in corresponding International Application No. PCT/US2011/023338.
Invitation to Pay Additional Fees and Partial Search Report mailed May 4, 2011 in corresponding International Application No. PCT/US2011/023283.
International Preliminary Report on Patentability mailed May 18, 2012 in corresponding International Application No. PCT/US2011/023283.
Written Opinion mailed May 16, 2012 in corresponding International Application No. PCT/US2011/023338.
International Preliminary Report on Patentability mailed Jul. 5, 2012 in corresponding International Application No. PCT/US2011/023338.
International Search Report and Written Opinion mailed May 31, 2012 in corresponding International Application No. PCT/US2011/043213.
Witzeman and Agreda in "Acetic Acid and its Derivatives,", Marcel Dekker, NY, 1992, p. 271.
US Office Action mailed May 3, 2012 in corresponding U.S. Appl. No. 12/833,737.
International Search Report and Written Opinion mailed Jun. 11, 2012 in corresponding International Application No. PCT/US2012/020977.
Gursahani et al., "Reaction kinetics measurements and analysis of reaction pathways for conversions of acetic acid, ethanol, and ethyl acetate over silica-supported Pt", Applied Catalysis A: General 222 (2001) 369-392.
Invitation to Pay Fees mailed Mar. 13, 2012 in corresponding International Application No. PCT/US2012/020977.
International Search Report and Written Opinion mailed Mar. 14, 2012 in corresponding International Application No. PCT/US2012/020979.
Pestman et al., Identification of the Active Sites in the Selective Hydrogenation of Acetic Acid to Acetaldehyde on Iron Oxide Catalysts, Journal of Catalysis 174:142-152 (1998).
International Search Report and Written Opinion for PCT/US2011/043310 dated Feb. 23, 2012.
Subramani et al. "A Review of Recent Literature to Search for an Efficient Catalytic Process for the Conversion of Syngas to Ethanol," Energy & Fuels, 2008, vol. 22, pp. 814-839.
Spivey et al., "Heterogeneous catalytic synthesis of ethanol from biomass-dervied syngas," Chemical Society Review, 2007, vol. 36, pp. 1514-1528.
Michael Gauβ, et al., Applied Homogeneous Catalysis with Organometallic Compounds: A Comprehensive Handbook in two Volume, Chapter 2.1, p. 27-200, (1st ed., 1996).
Juran et al., "Convert Methanol to Ethanol", Hydrocarbon Processing, Oct. 1985, pp. 85-87.
Zhang et al., "Hydrogenation of Ethyl Acetate to Ethanol over Ni-Based Catalysts Obtained from Ni/Ai Hydrotalcite-Like Compounds", Molecules, 2010, 15, 5139-5152.
International Search Report and Written Opinion mailed Jul. 12, 2012 in corresponding International Application No. PCT/US2012/035166.
Rachmady, Acetic Acid Reduction by H2 on Bimetallic Pt-Fe Catalysts, Journal of Catalysis 209, 87-98, Apr. 1, 2002, Elsevier Science (USA).
J. Jones, et al., "The Cativa™ Process for the Manufacture of Acetic Acid", Platinum Metals Review, vol. 44, No. 3, pp. 94-104 (Jul. 2000).
Hilmen, Separation of Azeotropic Mixtures: Tools for Analysis and Studies on Batch Distillation Operation (Nov. 2000) pp. 17-20.
International Search Report and Written Opinion mailed Jul. 6, 2012 in corresponding International Application No. PCT/US2011/059889.
Marian Simo et al., "Adsorption/Desorption of Water and Ethanol on 3A Zeolite in Near-Adiabatic Fixed Bed", Ind. Eng. Chem. Res., 2009, 48, 9247-9260.
N. Calvar et al., "Esterification of acetic acid with ethanol: Reaction kinetics and operation in a packed bed reactive distillation column", Chemical Engineering and Processing, 46 1317-1323, (2007).
Hidetoshi Kita et al., "Synthesis of a zeolite NaA membrane for pervaporation of water/organic liquid mixtures", Journal of Materials Science Letters, 14 (1995) 206-208.
International Search Report and Written Opinion mailed Jul. 12, 2012 in corresponding International Application No. PCT/US2012/035178.
International Search Report and Written Opinion mailed Mar. 13, 2012 in corresponding International Application No. PCT/US2011/042639.
Written Opinion mailed Aug. 10, 2012 in corresponding International Application No. PCT/US2011/042639.
International Preliminary Report on Patentability for PCT/US2011/043310 mailed Oct. 22, 2012.
International Preliminary Report on Patentability for PCT/US2011/042639 mailed Nov. 9, 2012.
International Preliminary Report on Patentability mailed Jan. 24, 2013 in corresponding International Application No. PCT/US2011/043213.

(56) References Cited

OTHER PUBLICATIONS

Alcala, et al., (2005). Experimental and DFT studies of the conversion of ethanol and acetic acid on PtSn-based catalysts, Journal of Physical Chemistry, 109(6), 2074-2085.

Amit M. Goda et al., DFT modeling of selective reduction of acetic acid to acetaldehyde on Pt-based bimetallic catalysts, 20th NAM, Houston, TX, Jun. 17-22, 2007 available online at http://www.nacatsoc.org/20nam/abstracts/O-S9-18.pdf.

Claus, et al., "Selective Hydrogenolysis of methyl and ethyl acetate in the gas phase on copper and supported Group VIII metal catalysts," Applied Catalysis A, 79, 1991, pp. 1-18.

English abstract for EP 0456647 A1, Nov. 21, 1991.

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Santori et al. (2000). Hydrogenation of carbonylic compounds on Pt/SiO2 catalysts modified with SnBu4, Studies in Surface Science and Catalysis, 130, 2063-2068.

ZeaChem, Inc., Technology Overview, Lakewood, Colorado www.zeachem.com, 2008.

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

HYDROGENOLYSIS OF ETHYL ACETATE IN ALCOHOL SEPARATION PROCESSES

CROSS REFERENCE TO RELATED APPLICATIONS

This application claims priority to U.S. Provisional App. No. 61/363,056, filed on Jul. 9, 2010, the entirety of which is incorporated herein by reference.

FIELD OF THE INVENTION

The present invention relates generally to processes for producing alcohol and, in particular, to forming an ethanol composition having a reduced ethyl acetate content.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition when conversion is incomplete, unreacted acid remains in the crude ethanol product, which must be removed to recover ethanol.

EP2060555 describes a process for producing ethanol where a carbonaceous feedstock is converted to synthesis gas which is converted to ethanoic acid, which is then esterified and which is then hydrogenated to produce ethanol. EP2072489 and EP2186787 also describe a similar process where the esters produced from esterification are fed to the alcohol synthesis reactor used to produce ethanol and methanol.

Therefore, a need remains for improving the recovery of ethanol from a crude product obtained by reducing alkanoic acids, such as acetic acid, and/or other carbonyl group-containing compounds.

SUMMARY OF THE INVENTION

In a first embodiment, the present invention is directed to a process for producing ethanol, comprising the steps of hydrogenating acetic acid in a first reactor in the presence of a catalyst to form a first crude ethanol product, separating at least a portion of the first crude ethanol product into an ethanol product stream and a derivative stream comprising ethyl acetate. The process may use one or more distillation column to separate the first crude ethanol product. The process further comprises reacting in a second reactor at least a portion of the derivative stream in the presence of hydrogen to form a second crude ethanol product. The second crude ethanol product may be fed to one of the distillation columns to separate ethanol.

In a second embodiment, the present invention is directed to a process for producing ethanol, comprising the steps of providing a first crude ethanol product comprising ethanol, acetic acid, ethyl acetate and water, separating at least a portion of the first crude ethanol product into an ethanol product stream and a derivative stream comprising ethyl acetate, and reacting at least a portion of the derivative stream in the presence of hydrogen to form a second crude ethanol product.

In a third embodiment, the present invention is directed to a process for producing ethanol, comprising the steps of hydrogenating acetic acid in a first reactor in the presence of a catalyst to form a first crude ethanol product, reacting in a second reactor at least a portion of the first crude ethanol product in the presence of hydrogen to form a second crude ethanol product, and separating at least a portion of the second crude ethanol product in one or more columns to obtain ethanol.

In a fourth embodiment, the present invention is directed to a process for producing ethanol, comprising the steps of hydrogenating acetic acid in a first reactor in the presence of a catalyst to form a first crude ethanol product, separating at least a portion of the first crude ethanol product in a first column into a first distillate comprising ethanol, water and ethyl acetate, and a first residue comprising acetic acid, separating at least a portion of the first distillate in a second column into a second distillate comprising ethyl acetate and a second residue comprising ethanol and water, optionally separating at least a portion of the second residue in a third column into a third distillate comprising ethanol and a third residue comprising water, optionally separating at least a portion of the second distillate in a fourth column into a fourth distillate comprising acetaldehyde and a fourth residue comprising ethyl acetate, and reacting in a second reactor at least a portion of the first distillate, at least a portion of the second distillate and/or at least a portion of the fourth residue in the presence of hydrogen to form a second crude ethanol product.

In a fifth embodiment, the present invention is directed to a process for purifying a first crude ethanol product, comprising the steps of providing the first crude ethanol product comprising ethanol, acetic acid, ethyl acetate and water, separating at least a portion of the first crude ethanol product in a first column into a first distillate comprising ethanol and a first residue comprising acetic acid, separating at least a portion of the first distillate in a second column into a second distillate comprising ethyl acetate and a second residue comprising ethanol and water, optionally separating at least a portion of the second residue in a third column into a third distillate comprising ethanol and a third residue comprising water, optionally separating at least a portion of the second distillate in a fourth column into a fourth distillate comprising acetaldehyde and a fourth residue comprising ethyl acetate, and reacting at least a portion of the first distillate, at least a portion of the second distillate and/or at least a portion of the fourth residue in the presence of hydrogen to form a second crude ethanol product.

In a sixth embodiment, the present invention is directed to a process for hydrogenolyzing ethyl acetate, comprising hydrogenating acetic acid in a reactor in the presence of a catalyst to form a first crude ethanol product; and reacting an ethyl acetate-containing stream in a hydrogenolysis unit under conditions effective to form a second crude ethanol product comprising more ethanol than the ethyl acetate-containing stream, wherein the ethyl acetate-containing stream is the first crude ethanol product or a derivative stream thereof.

BRIEF DESCRIPTION OF DRAWINGS

The invention may be more completely understood in consideration of the following detailed description of various embodiments of the invention in connection with the accompanying drawings, wherein like numerals designate similar parts.

DETAILED DESCRIPTION OF THE INVENTION

Introduction

Figure 1A:
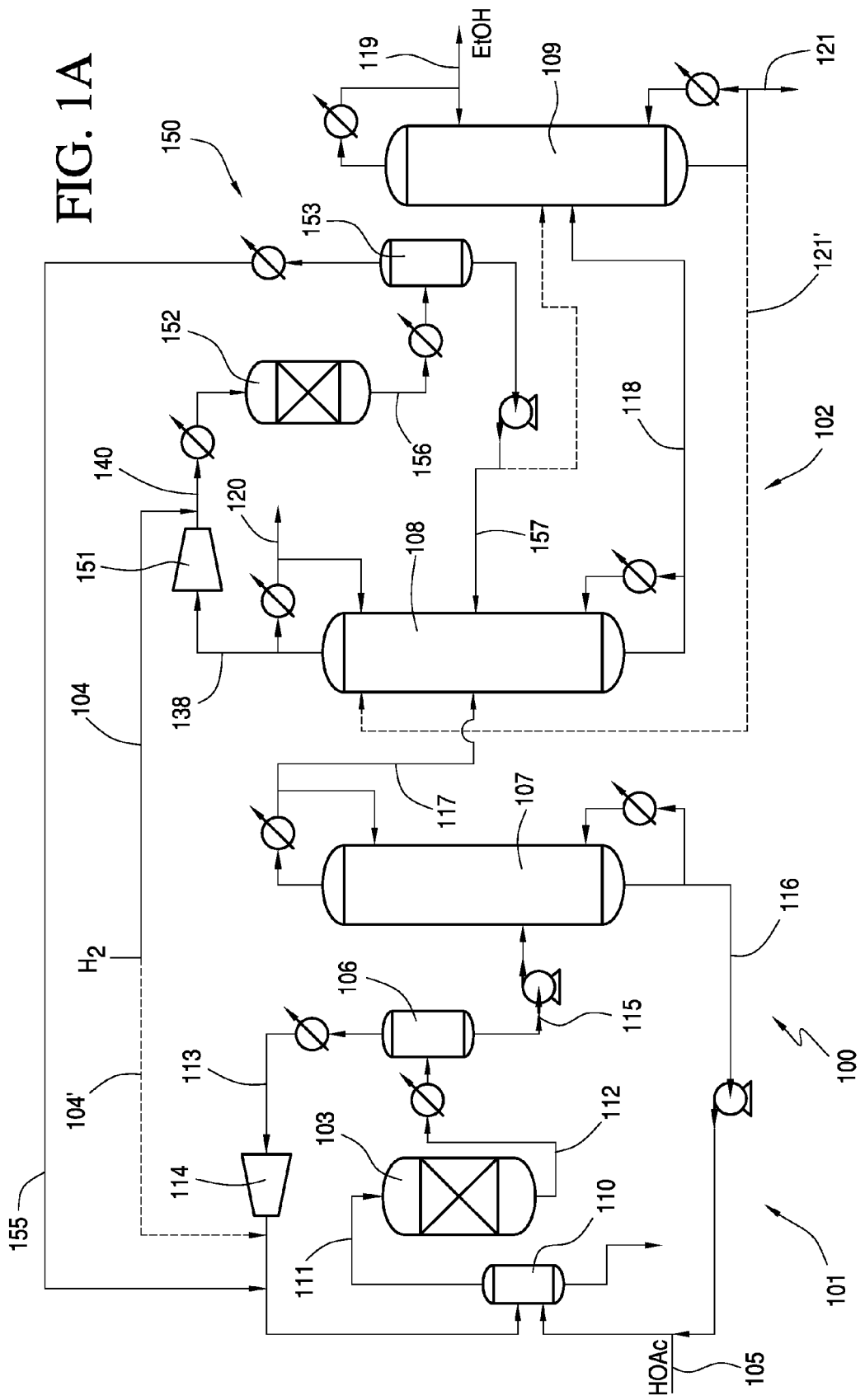
FIG. 1A is a schematic diagram of an ethanol production system that directs a vapor derivative stream to a hydrogenolysis reactor in accordance with one embodiment of the present invention.

The present invention relates generally to processes for forming ethanol in an ethanol production system wherein a stream comprising ethyl acetate is reacted with hydrogen, i.e. through hydrogenolysis, to form additional ethanol. The processes are particularly well-suited for ethanol production systems in which acetic acid is hydrogenated in the presence of a catalyst to form ethanol. The additional ethanol is in addition to the ethanol produced through hydrogenation. Embodiments of the present invention preferably increase or maximize ethanol yield and may also reduce waste streams that are purged from the system. The hydrogenolysis reaction is as follows:

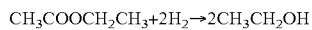

The processes of the present invention can be applied to a variety of ethanol production systems and beneficially may be used in applications for the recovery and/or purification of ethanol on an industrial scale. For example, various aspects of the present invention relate to processes for recovering and/or purifying ethanol produced by a process comprising hydrogenating acetic acid in the presence of a catalyst. In one embodiment, byproduct ethyl acetate, which may be produced during the hydrogenating of acetic acid and may be present in the crude ethanol product and/or a derivative stream of the crude product, is preferably reacted in the presence of hydrogen to form ethanol.

The hydrogenation of acetic acid to form ethanol and water may be represented by the following reaction:

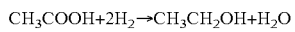

In theoretical embodiments where ethanol and water are the only products of the hydrogenation reaction, the crude ethanol product comprises 71.9 wt. % ethanol and 28.1 wt. % water. However, not all of the acetic acid fed to the hydrogenation reactor is typically converted to ethanol. Subsequent reactions of ethanol, such as esterification with acetic acid, may form other byproducts such as ethyl acetate. Ethyl acetate is a byproduct that reduces the yield of ethanol in the process. Ethyl acetate may also be produced by the directed hydrogenation of acetic acid. In preferred embodiments, the ethyl acetate is subjected to a hydrogenolysis reaction to advantageously consume ethyl acetate while producing additional ethanol.

Until the excess acetic acid, which is not converted to products in the hydrogenation reactor, is substantially removed from the crude ethanol product, e.g., in an acid separation column, the crude ethanol product is not at chemical equilibrium and the composition favors esterification of ethanol with acetic acid to form ethyl acetate and water. In some embodiments, it may be advantageous to esterify the unreacted acetic acid initially followed by a subsequent hydrogenolysis of the ethyl acetate.

In one embodiment, one or more of the derivative streams obtained by recovering and/or purifying a crude ethanol product is reacted with hydrogen through hydrogenolysis. The derivative stream comprises ethyl acetate and optionally one or more of ethanol, acetic acid, acetaldehyde, which includes acetals such as diethyl acetal, and water. To provide an improved efficiency by using the hydrogenolysis reactor, the derivative stream preferably comprises at least 5 wt. % ethyl acetate, e.g., at least 15 wt. % or at least 40 wt. %. In one embodiment, the derivative stream comprises ethyl acetate and acetaldehyde. In another embodiment, the derivative stream comprises ethyl acetate, acetaldehyde, and ethanol. In yet another embodiment, the derivative stream comprises ethyl acetate, acetaldehyde, ethanol, and water. In still another embodiment, the derivative stream comprises ethyl acetate, acetaldehyde, ethanol, water and acetic acid. Each of the components in the derivative stream may be obtained from separate streams and mixed. In addition, the one or more derivative streams to be reacted in the hydrogenolysis reactor preferably comprise substantially no acetic acid, e.g., less than 2 wt. % or less than 0.5 wt. %. In other embodiments, the amount of ethanol in the derivative stream to be reacted via hydrogenolysis preferably comprises minor amounts of ethanol, e.g., less than 20 wt. %, or less than 10 wt. %.

In one embodiment, the crude ethanol product may be fed to a hydrogenolysis reactor. In such embodiments, the derivative stream to be reacted may comprise ethyl acetate, acetic acid, ethanol, and water, as discussed above. Depending on the reaction conditions and catalyst, further hydrogenation of acetic acid and/or other components, such as acetaldehyde, may occur in the hydrogenolysis reactor forming additional ethanol.

According to one embodiment of the invention, the derivative stream is passed through a hydrogenolysis reactor, which comprises a catalyst. Suitable hydrogenolysis catalysts include copper supported on silica or copper oxide supported on magnesia-silica, Raney copper catalysts, Group VIII supported catalysts, and catalysts as described below in connection with the hydrogenation process. Further catalysts are described in U.S. Pat. No. 5,198,592, and Claus, et al., "Selective Hydrogenolysis of methyl and ethyl acetate in the gas phase on copper and supported Group VIII metal catalysts," Applied Catalysts A: General, Vol. 79 (1991) pages 1-18, both of which are hereby incorporated by reference.

Hydrogenation Process

The hydrogenation of acetic acid to form ethanol is preferably conducted in the presence of a hydrogenation catalyst. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst may favor the formation of ethyl acetate and mixtures of ethyl acetate and ethanol. Such catalysts are described in U.S. Pub. Nos. 2010/0029980; 2010/0121114; 2010/0197959; and 2010/0197485 and pending U.S. application Ser. No. 12/699,003, the entire contents and disclosures of which are incorporated by reference. One catalyst for making ethyl acetate includes a combination of a first metal selected from the group consisting of nickel, platinum and palladium and a second metal selected from the group consisting of molybdenum, rhenium, zirconium, zinc, tin, copper, and cobalt on a support. A particular catalyst that may be suited for producing ethyl acetate comprises platinum, tin and at least one support, wherein the molar ratio of platinum to tin is less than 0.4:0.6 or greater than 0.6:0.4. Another suitable catalyst comprises palladium, rhenium, and at least one support, wherein the molar ratio of rhenium to palladium is less than 0.7:0.3 or greater than 0.85:0.15.

In one exemplary embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. When the first metal comprises platinum, it is preferred that the catalyst comprises platinum in an amount less than 5 wt. %, e.g., less than 3 wt. % or less than 1 wt. %, due to the high demand for platinum.

As indicated above, the catalyst optionally further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

In certain embodiments where the catalyst includes two or more metals, e.g., a first metal and a second metal, the first metal optionally is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 to 4 wt. %, e.g., from 0.1 to 3 wt. %, or from 0.1 to 2 wt. %.

In addition to one or more metals, the exemplary catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 wt. % to 99.9 wt. %, e.g., from 78 wt. % to 97 wt. %, or from 80 wt. % to 95 wt. %. In preferred embodiments that use a modified support, the support modifier is present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $CO_2O_3$, and $Bi_2O_3$.

In another embodiment, the support modifier may be a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain N or Pro. The Saint-Gobain N or Pro SS61138 silica exhibits the following properties: contains approximately 95 wt. % high surface area silica; surface area of about 250 $m^2/g$; median pore diameter of about 12 nm; average pore volume of about 1.0 $cm^3/g$ as measured by mercury intrusion porosimetry and a packing density of about 0.352 $g/cm^3$ (22 $lb/ft^3$).

A preferred silica/alumina support material is KA-160 silica spheres from Sud Chemie having a nominal diameter of about 5 mm, a density of about 0.562 g/ml, an absorptivity of about 0.583 g $H_2O$/g support, a surface area of about 160 to 175 $m^2/g$, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation step optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^-$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%.

Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 40 wt. % water. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 10 to 60 | 15 to 50 | 25 to 50 |
| Acetic Acid | 0 to 90 | 5 to 80 | 15 to 70 | 20 to 70 |
| Water | 5 to 40 | 5 to 30 | 10 to 30 | 10 to 26 |
| Ethyl Acetate | 0.01 to 30 | 0.05 to 20 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

As indicated above, the hydrogenation process preferably forms primarily ethanol and a minor amount of ethyl acetate.

In other embodiments, the catalyst selected for hydrogenating acetic acid may favor the formation of ethyl acetate, i.e., have a greater selectivity for ethyl acetate than for ethanol, and particularly may favor formation of mixtures of ethanol and ethyl acetate. In these embodiments, the crude product may have more ethyl acetate, on a weight basis, than the crude ethanol product as described above in Table 1. The processes of the present invention advantageously can tolerate increased formation of ethyl acetate since ultimately the ethyl acetate will be converted to ethanol in the hydrogenolysis step.

In one embodiment, the crude ethanol product may comprise acetic acid in an amount less than 20 wt. %, e.g., of less than 15 wt. %, less than 10 wt. % or less than 5 wt. %. In embodiments having lower amounts of acetic acid, the conversion of acetic acid is preferably greater than 75%, e.g., greater than 85% or greater than 90%. In addition, the selectivity to ethanol may also be preferably high, and is preferably greater than 75%, e.g., greater than 85% or greater than 90%.

Purification System

Figure 1B:
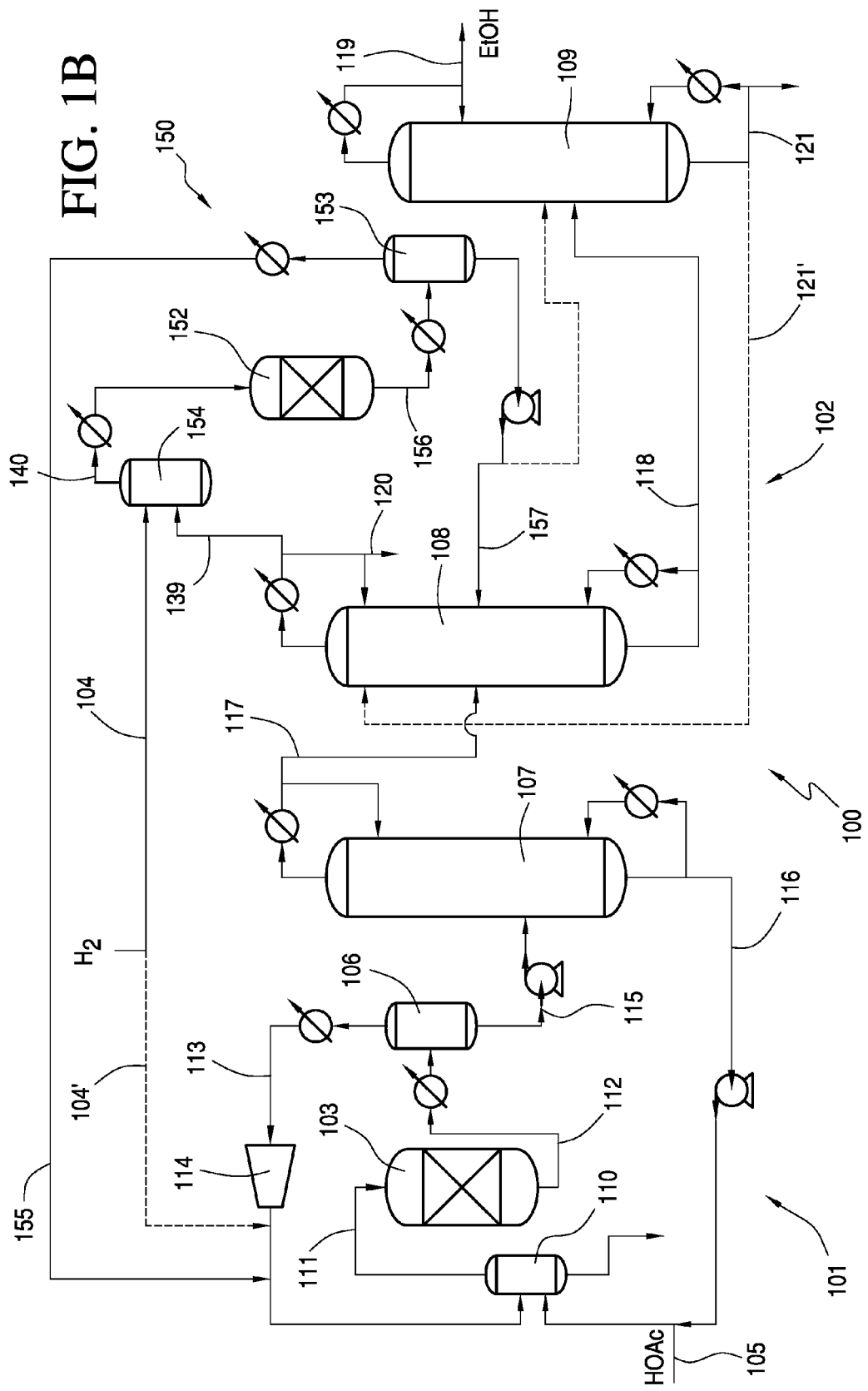
FIG. 1B is a schematic diagram of an ethanol production system that directs a liquid derivative stream to a hydrogenolysis reactor in accordance with one embodiment of the present invention.
Figure 2:
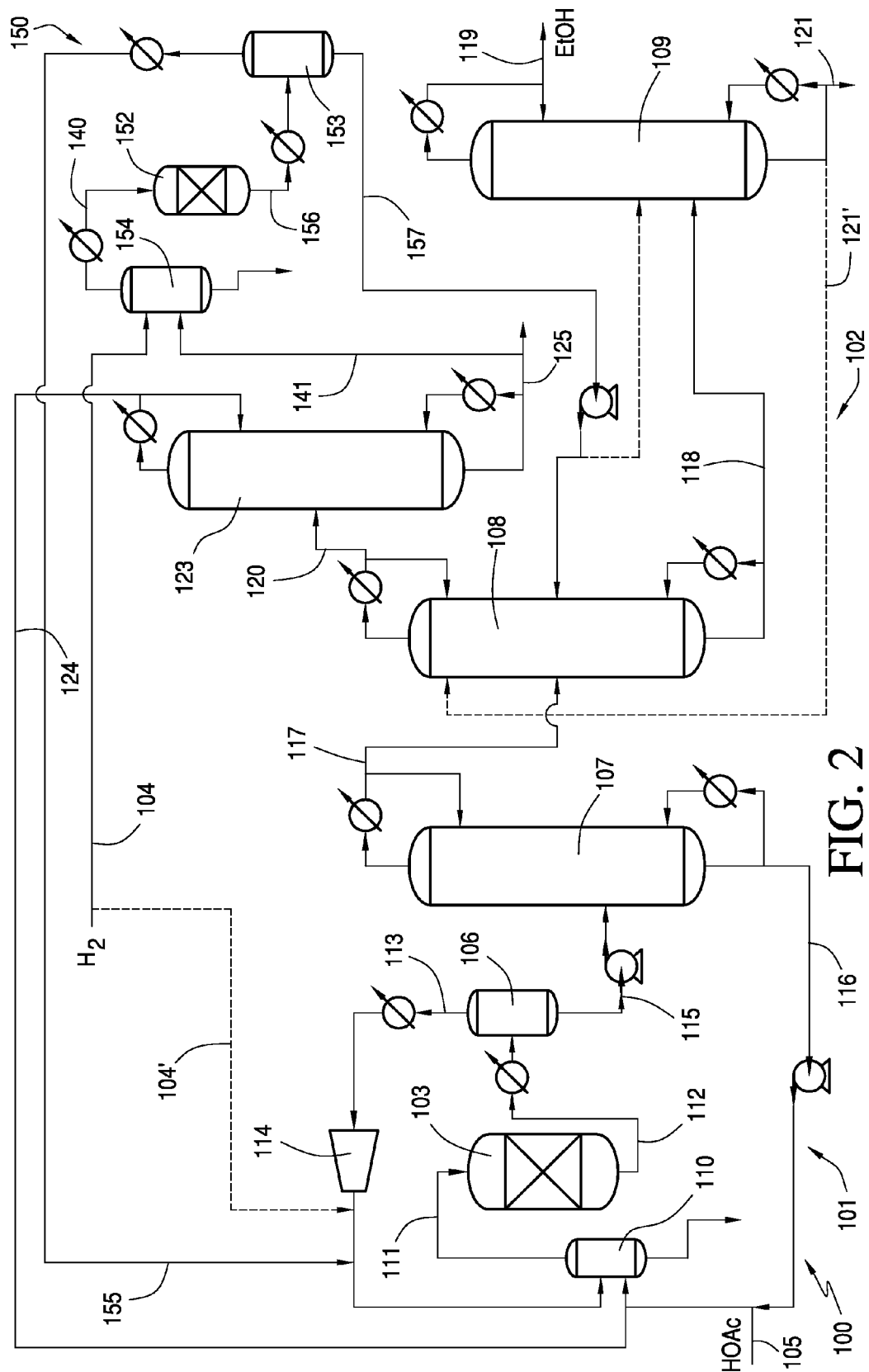
FIG. 2 is a schematic diagram of an ethanol production system having a column to remove acetaldehyde that directs a liquid derivative stream to a hydrogenolysis reactor in accordance with one embodiment of the present invention.

FIGS. 1A, 1B, and 2 show a hydrogenation system 100 suitable for the hydrogenation of acetic acid, the hydrogenolysis of ethyl acetate and separating ethanol from the crude reaction mixture according to one embodiment of the invention. System 100 comprises reaction zone 101, separation zone 102, and hydrogenolysis zone 150. Reaction zone 101 comprises reactor 103, acetic acid feed line 105, and vaporizer 110. In FIGS. 1A and 1B, separation zone 102 comprises separator 106, first column 107, second column 108, and third column 109. In FIG. 2, separation zone 102 comprises separator 106, first column 107, second column 108, third column 109, and fourth column 123. In FIG. 1A, hydrogenolysis zone 150 comprises hydrogen feed line 104, compressor 151, hydrogenolysis reactor 152, and flasher 153. In FIG. 1B and FIG. 2, the hydrogenolysis zone comprises hydrogen feed line 104, hydrogenolysis reactor 152, flasher 153 and vaporizer 154.

As shown, hydrogen is preferably fed directly to hydrogenolysis zone 150 via line 104. In embodiments of the present invention there is substantially no hydrogen in the derivative streams from the separation zone 102 that are fed to the hydrogenolysis zone 150 and fresh hydrogen via line 104 is preferably added to hydrogenolysis zone 150. The excess hydrogen from hydrogenolysis zone 150 may be flashed and fed to the reaction zone 101 via line 155. In one embodiment, the hydrogen fed to hydrogenation reactor 103 is fed without increasing the pressure from the feed source. In addition, the hydrogenolysis reactor 152 preferably does not have a gas recycle loop. Optionally, hydrogen may also be fed directly to reaction zone 101 via line 104'. In preferred embodiments, hydrogen from lines 104' and/or 155 may be added downstream of compressor 114. Hydrogen from the reaction zone 101 in line 113 may also be combined with the hydrogen from line 104' and/or 155.

In other embodiments, there may be separate hydrogen sources for the hydrogenation reactor 103 and hydrogenolysis reactor 152.

In one embodiment, hydrogen may be fed to the reaction zone 101 via line 104' and the unreacted hydrogen is flashed and separated from the crude ethanol product and fed to the hydrogenolysis reactor 152.

Hydrogen, either fed directly from line 104', indirectly from line 155 or a combination of both, and acetic acid via line 105 may be fed to a vaporizer 110 in reaction zone 101. In one embodiment, hydrogen and acetic acid may be combined and jointly fed to the vaporizer 110, e.g., in one stream containing both hydrogen and acetic acid. Vaporizer 110 generates a vapor feed stream in line 111 that is directed to reactor 103. The temperature of the vapor feed stream in line 111 is preferably from 100° C. to 350° C., e.g., from 120° C. to 310° C. or from 150° C. to 300° C. Any feed that is not vaporized is removed from vaporizer 110, as shown, and may be recycled or discarded. In addition, although FIGS. 1A, 1B, and 2 represent line 111 being directed to the top of reactor 103, line 111 may be directed to the side, upper portion, or bottom of reactor 103. Further modifications and additional components to reaction zone 101 are described below.

Reactor 103 contains the catalyst that is used in the hydrogenation of the carboxylic acid, preferably acetic acid, to form ethanol. In one embodiment, one or more guard beds (not shown) may be used upstream of the reactor, optionally upstream of vaporizer 110, to protect the catalyst from poisons or undesirable impurities contained in the feed or return/recycle streams. Such guard beds may be employed in the vapor or liquid streams. Suitable guard bed materials are known in the art and include, for example, carbon, silica, alumina, ceramic, or resins. In one aspect, the guard bed media is functionalized, e.g., silver functionalized, to trap particular species such as sulfur or halogens. During the hydrogenation process, a crude ethanol product stream is withdrawn, preferably continuously, from reactor 103 via line 112.

The crude ethanol product stream may be condensed and fed to separator 106, which, in turn, provides a vapor stream 113 and a liquid stream 115. Suitable separators 106 include one or more flashers or knockout pots. The separator 106 may operate at a temperature of from 20° C. to 250° C., e.g., from 30° C. to 225° C. or from 60° C. to 200° C. The pressure of separator 106 may be from 50 kPa to 2000 kPa, e.g., from 75 kPa to 1500 kPa or from 100 kPa to 1000 kPa. Optionally, the crude ethanol product in line 112 may pass through one or more membranes, not shown, to separate hydrogen and/or other non-condensable gases therefrom.

The vapor stream exiting the separator 106 may comprise hydrogen and hydrocarbons, which may be purged and/or returned to reaction zone 101 via line 113. As shown, the returned portion of the vapor stream 113 may be combined with the hydrogen feed from lines 104' and/or 155 downstream of compressor 114 and co-fed to vaporizer 110. In some embodiments, the returned vapor stream 113 may be compressed before being combined with the hydrogen feed.

The liquid from separator 106 is withdrawn and pumped via line 115 to the side of first column 107, also referred to as the acid separation column. In one embodiment, the contents of line 115 are substantially similar to the crude ethanol product obtained from the reactor, except that the composition has substantially no hydrogen, carbon dioxide, methane or ethane, which are removed by the separator 106. Exemplary components of liquid in line 115 are provided in Table 2. Liquid stream 115 may contain other components not specifically listed in Table 2.

TABLE 2

| COLUMN FEED COMPOSITION (Liquid Stream 115) | | | |
|---|---|---|---|
|  | Conc. (wt. %) | Conc. (wt. %) | Conc. (wt. %) |
| Ethanol | 5 to 70 | 10 to 60 | 15 to 50 |
| Acetic Acid | <90 | 5 to 80 | 15 to 70 |
| Water | 5 to 35 | 5 to 30 | 10 to 30 |
| Ethyl Acetate | <20 | 0.001 to 15 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout present application are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, the liquid stream, e.g., line 115, may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

When the content of acetic acid in line 115 is less than 5 wt. %, the acid separation column 107 may be skipped and line 115 may be introduced directly to second column 108, also referred to herein as a light ends column. In addition, column 107 may be operated to initially remove a substantial portion of water as the residue.

In the embodiment shown in FIG. 1A, line 115 is introduced in the lower part of first column 107, e.g., lower half or lower third. In first column 107, unreacted acetic acid, a portion of the water, and other heavy components, if present, are removed from the composition in line 115 and are withdrawn, preferably continuously, as residue. Some or all of the first residue may be directly or indirectly returned and/or recycled back to reaction zone 101 via line 116. Recycling the acetic acid in line 116 to the vaporizer 110 may reduce the amount of heavies that need to be purged from vaporizer 110. Reducing the amount of heavies to be purged may improve efficiencies of the process while reducing byproducts. Optionally, acetic acid in line 116 may be processed using a weak acid recovery system to remove water in the line 116 and return a dry acetic acid composition to vaporizer 110.

Optionally, a substantial portion of the water from the crude ethanol product, e.g., from 30 to 90 wt. %, may be removed in residue in line 116. Depending on the composition, the residue stream may be: (i) entirely or partially recycled to the hydrogenation reactor, (ii) separated into acid and water streams, (iii) treated with a solvent in a weak acid recovery process, (iv) reacted with an alcohol to consume the unreacted acetic acid, or (v) disposed to a waste water treatment facility.

In another embodiment, unreacted acetic acid, water, and other heavy components, if present, are removed from the composition in line 115 and are withdrawn, preferably continuously, as the residue of column 107. In some embodiments, especially with higher conversions of acetic acid of at least 80%, or at least 90%, it may be beneficial to remove a majority of water in the residue of column 107 along with substantially all of the acetic acid. Residue stream 116 may be recycled to reaction zone 101. In addition, a portion of the water in residue stream 116 may be separated and purged with the acid rich portion being returned to reaction zone 201. In other embodiments, the residue stream 116 may be a dilute acid stream that may be treated in a weak acid recovery system or sent to a reactive distillation column to convert the acid to esters.

Reverting to FIG. 1A, first column 107 also forms an overhead distillate, which is withdrawn in line 117, and which may be condensed and refluxed, for example, at a ratio of from 10:1 to 1:10, e.g., from 3:1 to 1:3 or from 1:2 to 2:1.

The columns shown in the figures may comprise any distillation column capable of performing the desired separation and/or purification. Each column preferably comprises a tray column having from 1 to 150 trays, e.g., from 10 to 100, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in FIGS. 1A, 1B, and 2. As shown in FIGS. 1A, 1B, and 2, heat may be supplied to the base of each column or to a circulating bottoms stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and flasher are shown, additional reactors, flashers, condensers, heating elements, and other components may be used in embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in any of the columns may vary. As a practical matter, pressures from 10 kPa to 3000 kPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, that the temperature at a given location in an operating distillation column is dependent on the composition of the material at that location and the pressure of column. In addition, feed rates may vary depending on the size of the production process and, if described, may be generically referred to in terms of feed weight ratios.

When column 107 is operated under about 170 kPa, the temperature of the residue exiting in line 116 from column 107 preferably is from 90° C. to 130° C., e.g., from 95° C. to 120° C. or from 100° C. to 115° C. The temperature of the distillate exiting in line 117 from column 107 preferably is from 60° C. to 90° C., e.g., from 65° C. to 85° C. or from 70° C. to 80° C. In other embodiments, the pressure of first column 107 may range from 0.1 kPa to 510 kPa, e.g., from 1 kPa to 475 kPa or from 1 kPa to 375 kPa. Distillate and residue compositions for first column 107 for one exemplary embodiment of the present invention are provided in Table 3. Note that these compositions may change depending on acetic acid conversion, the operation of the column, and whether a majority of the water is removed in the residue. It should be understood that the distillate and residue may also contain other components, not listed, such as components in the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

| FIRST COLUMN | | | |
|---|---|---|---|
| | Conc. (wt. %) | Conc. (wt. %) | Conc. (wt. %) |
| Distillate | | | |
| Ethanol | 20 to 75 | 30 to 70 | 40 to 65 |
| Water | 10 to 40 | 15 to 35 | 20 to 35 |
| Acetic Acid | <2 | 0.001 to 0.5 | 0.01 to 0.2 |
| Ethyl Acetate | <60 | 5.0 to 40 | 10 to 30 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue | | | |
| Acetic Acid | 60 to 100 | 70 to 95 | 85 to 92 |
| Water | <30 | 1 to 20 | 1 to 15 |
| Ethanol | <1 | <0.9 | <0.07 |

As discussed above, in one embodiment, a substantial portion of the water from the crude ethanol product in line 115 may be separated into the residue in line 116. As a result the water concentrations in Table 3 for the residue would be higher, e.g. up to 90 wt. %., or up to 75 wt. %. Particularly at high conversions, the residue of the first column 107 may comprise a significantly greater concentration of water than is indicated in Table 3. In other embodiments, the residue stream 116 may be a dilute acid stream that may be treated in a weak acid recovery system or sent to a reactive distillation column to convert the acid to esters.

As shown in Table 3, without being bound by theory, it has surprisingly and unexpectedly been discovered that when any amount of acetal is detected in the feed that is introduced to the acid separation column (first column 107), the acetal appears to decompose in the column such that less or even no detectable amounts are present in the distillate and/or residue.

Depending on the reaction conditions, the crude ethanol product exiting reactor 103 in line 112 may comprise ethanol, acetic acid (unconverted), ethyl acetate, and water. After exiting reactor 103, a non-catalyzed equilibrium reaction may occur between the components contained in the crude ethanol product until it is added to separator 106 and/or first column 107. This equilibrium reaction tends to drive the crude ethanol product to an equilibrium between ethanol/acetic acid and ethyl acetate/water, as shown below.

EtOH+HOAc⇌EtOAc+H₂O

In the event the crude ethanol product is temporarily stored, e.g., in a holding tank, prior to being directed to separation zone 102, extended residence times may be encountered. Generally, the longer the residence time between reaction zone 101 and separation zone 102, the greater the formation of ethyl acetate. For example, when the residence time between reaction zone 101 and separation zone 102 is greater than 5 days, significantly more ethyl acetate may form at the expense of ethanol. Thus, shorter residence times between reaction zone 101 and separation zone 102 are generally preferred in order to maximize the amount of ethanol formed. In one embodiment, a holding tank (not shown), is included between the reaction zone 101 and separation zone 102 for temporarily storing the liquid component from line 115 for up to 5 days, e.g., up to 1 day, or up to 1 hour. In a preferred embodiment no tank is included and the condensed liquids are fed directly to the first distillation column 107. In addition, the rate at which the non-catalyzed reaction occurs may increase as the temperature of the crude ethanol product, e.g., in line 115, increases. These reaction rates may be particularly problematic at temperatures exceeding 30° C., e.g., exceeding 40° C. or exceeding 50° C. Thus, in one embodiment, the temperature of liquid components in line 115 or in the optional holding tank is maintained at a temperature less than 40° C., e.g., less than 30° C. or less than 20° C. One or more cooling devices may be used to reduce the temperature of the liquid in line 115.

As discussed above, a holding tank (not shown) may be included between the reaction zone 101 and separation zone 102 for temporarily storing the liquid component from line 115, for example from 1 to 24 hours, optionally at a temperature of about 21° C., and corresponding to an ethyl acetate formation of from 0.01 wt. % to 1.0 wt. % respectively. In addition, the rate at which the non-catalyzed reaction occurs may increase as the temperature of the crude ethanol product is increased. For example, as the temperature of the crude ethanol product in line 115 increases from 4° C. to 21° C., the rate of ethyl acetate formation may increase from about 0.01 wt. % per hour to about 0.05 wt. % per hour. Thus, in one embodiment, the temperature of liquid components in line 115 or in the optional holding tank is maintained at a temperature less than 21° C., e.g., less than 4° C. or less than −10° C.

The distillate, e.g., overhead stream, of column 107 optionally is condensed and refluxed as shown in FIG. 1A, preferably, at a reflux ratio of 1:5 to 10:1. The distillate in line 117 preferably comprises ethanol, ethyl acetate, and water, along with other impurities.

The first distillate in line 117 is introduced to the second column 108, also referred to as the "light ends column," preferably in the top part of column 108, e.g., top half or top third. Second column 108 may be a tray column or a packed column. In one embodiment, second column 108 is a tray column having from 5 to 70 trays, e.g., from 15 to 50 trays or from 20 to 45 trays. As one example, when a 30 tray column is utilized without water extraction, line 117 may be introduced at tray 2. In one embodiment, the second column 108 may be an extractive distillation column. In such embodiments, an extraction agent, such as for example water, may be added to second column 108. If the extraction agent comprises water, it may be obtained from an external source or from an internal return/recycle line from one or more of the other columns. Optionally, the extraction agent is obtained by recycling a portion of the third residue 121'.

Other suitable extractive agents may include, for example, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or a combination thereof.

Although the temperature and pressure of second column 108 may vary, when at about 20 kPa to 70 kPa, the temperature of the second residue exiting in line 118 from second column 108 preferably is from 30° C. to 75° C., e.g., from 35° C. to 70° C. or from 40° C. to 65° C. The temperature of the second distillate exiting in line 120 from second column 108 preferably is from 20° C. to 55° C., e.g., from 25° C. to 50° C. or from 30° C. to 45° C. Column 108 may operate at a reduced pressure, near or at vacuum conditions, to further favor separation of ethyl acetate and ethanol. In other embodiments, the pressure of second column 108 may range from 0.1 kPa to 510 kPa, e.g., from 1 kPa to 475 kPa or from 1 kPa to 375 kPa. Exemplary components of the distillate and residue compositions for second column 108 are provided in Table 4 below. It should be understood that the distillate and residue may also contain other components, not listed, such as components in the feed.

TABLE 4

| SECOND COLUMN | | | |
|---|---|---|---|
| | Conc. (wt. %) | Conc. (wt. %) | Conc. (wt. %) |
| Distillate | | | |
| Ethyl Acetate | 10 to 90 | 25 to 90 | 50 to 90 |
| Acetaldehyde | 1 to 25 | 1 to 15 | 1 to 8 |
| Water | 1 to 25 | 1 to 20 | 4 to 16 |
| Ethanol | <30 | 0.001 to 15 | 0.01 to 5 |
| Acetal | <5 | 0.001 to 2 | 0.01 to 1 |
| Residue | | | |
| Water | 30 to 70 | 30 to 60 | 30 to 50 |
| Ethanol | 20 to 75 | 30 to 70 | 40 to 70 |
| Ethyl Acetate | <3 | 0.001 to 2 | 0.001 to 0.5 |
| Acetic Acid | <0.5 | 0.001 to 0.3 | 0.001 to 0.2 |

The weight ratio of ethanol in the second residue to ethanol in the second distillate preferably is at least 2:1, e.g., at least 3:1, at least 8:1, at least 10:1 or at least 15:1. The weight ratio of ethyl acetate in the second residue to ethyl acetate in the second distillate preferably is less than 0.4:1, e.g., less than 0.2:1 or less than 0.1:1. In embodiments that use an extractive column with water as an extraction agent as the second column 108, the weight ratio of ethyl acetate in the second residue to ethyl acetate in the second distillate preferably is less than 0.1:1. In some embodiments where water is removed in the first column 107, the water concentration in the second distillate and second residue may be lower than indicated in Table 4.

As shown in FIGS. 1A, 1B, and 2, the second residue from the bottom of second column 108, which comprises ethanol and water, is fed via line 118 to third column 109, also referred to as the "product column." More preferably, the second residue in line 118 is introduced in the lower part of third column 109, e.g., lower half or lower third. Third column 109 recovers ethanol, which preferably is substantially pure other than the azeotropic water content, as the distillate in line 119. The distillate of third column 109 preferably is refluxed, for example, at a reflux ratio of from 1:10 to 10:1, e.g., from 1:3 to 3:1 or from 1:2 to 2:1. The third residue in line 121, which preferably comprises primarily water, is preferably removed from the system 100 or may be partially directed to any portion of the system 100, optionally to the second column 108 via line 121'. Third column 109 is preferably a tray column as described above and preferably operates at atmospheric pressure. The temperature of the third distillate exiting in line 119 from third column 109 preferably is from 60° C. to 110° C., e.g., from 70° C. to 100° C. or from 75° C. to 95° C. The temperature of the third residue exiting from third column 109 preferably is from 70° C. to 115° C., e.g., from 80° C. to 110° C. or from 85° C. to 105° C. Exemplary components of the distillate and residue compositions for third column 109 are provided in Table 5 below. It should be understood that the distillate and residue may also contain other components, not listed, such as components in the feed.

TABLE 5

THIRD COLUMN

|  | Conc. (wt. %) | Conc. (wt. %) | Conc. (wt. %) |
|---|---|---|---|
| Distillate |  |  |  |
| Ethanol | 75 to 96 | 80 to 96 | 85 to 96 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| Residue |  |  |  |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In one embodiment, one or more side streams may remove impurities from any of the columns 107, 108 and/or 109 in the system 100. Preferably at least one side stream is used to remove impurities from the third column 109. The impurities may be purged and/or retained within the system 100.

The third distillate in line 119 may be further purified to form an anhydrous ethanol product stream, i.e., "finished anhydrous ethanol," using one or more additional separation systems, such as, for example, distillation columns (e.g., a finishing column) or molecular sieves.

Optionally, when the water concentration of the second residue in line 118 is sufficiently low, e.g. less than 20 wt. % or less than 10 wt. %, water may be removed using an adsorption unit, membrane, molecular sieves, extractive distillation, or a combination thereof. The adsorption unit may employ a suitable adsorption agent such as zeolite 3A or 4A. In one preferred embodiment, adsorption unit is a pressure swing adsorption (PSA) unit that is operated at a temperature from 30° C. to 160° C., e.g., from 80° C. to 140° C., and a pressure of from 0.01 kPa to 550 kPa, e.g., from 1 kPa to 150 kPa. The PSA unit may comprise two to five beds.

Returning to second column 108, the second distillate preferably is refluxed as shown in FIGS. 1A and 1B, for example, at a reflux ratio of from 1:30 to 30:1, e.g., from 1:5 to 5:1 or from 1:3 to 3:1.

In FIG. 1A, a gaseous portion of the second distillate in line 120 is directed via line 138 to the hydrogenolysis zone 150. A portion of the second distillate in line 120 may also be purged or refluxed. The gaseous portion of the second distillate may be fed to compressor 151. The compressed gaseous portion in line 140 is co-fed with hydrogen feed stream 104 and directed to the hydrogenolysis reactor 152. Optionally, hydrogen feed stream 104 may be fed to the compressor 151 to form the compressed gaseous portion 140. In addition, gaseous portion in line 138 may also be pre-heated before being fed to compressor 151. The compressed gaseous portion and hydrogen in line 140 may be preheated to a temperature of at least 150° C., e.g., at least 200° C. or at least 250° C. before being fed to hydrogenolysis reactor 152, provided that the feed, i.e., compressed gaseous portion 140, remains in the vapor phase and above the dew point.

The hydrogenolysis reactor 152 preferably comprises a hydrogenolysis catalyst. The reactants, namely the ethyl acetate in the gaseous portion of the second distillate, reacts in the presence of hydrogen and the catalyst to form ethanol. Suitable hydrogenolysis catalysts include copper support on silica or copper oxide supported on magnesia-silica, Raney copper catalysts, Group VIII supported catalysts, and catalysts as described above with respect to the hydrogenation reaction. Further catalysts are described in U.S. Pat. No. 5,198,592, and Claus, et al., "Selective Hydrogenolysis of methyl and ethyl acetate in the gas phase on copper and supported Group VIII metal catalysts," Applied Catalysts A: General, Vol. 79 (1991) pages 1-18, which are incorporated herein by reference. The reaction conditions in the hydrogenolysis reactor 152 may vary, but the reaction is preferably conducted at a temperature of from 150° C. to 350° C., e.g., from 200° C. to 300° C. or from 225° C. to 290° C. and a pressure of from 1 MPa to 6 MPa, e.g., from 2 MPa to 5 MPa or from 3 MPa to 4.5 MPa. The hydrogenolysis reaction is preferably conducted continuously in the gas phase. The hydrogenolysis reactor 152 is preferably operated under conditions effective to convert at least 40% of the ethyl acetate to ethanol, e.g., at least 80% or at least 90%. The hydrogenolysis reaction may be conducted with excess molar amounts of hydrogen and preferably the molar ratio of hydrogen to ethyl acetate is greater than 10:1, e.g., greater than 15:1, or greater than 20:1. In one preferred embodiment, the molar ratio is about 25:1. The excess hydrogen may be removed and fed to the hydrogenation reactor 103.

The crude reaction product of the hydrogenolysis reactor 152 is continuously withdrawn via line 156. In one embodiment, the crude reaction product comprises at least 5% less ethyl acetate than the gaseous portion of the second distillate in via 138, e.g., at least 75% less ethyl acetate or at least 90% less ethyl acetate. In another embodiment, the crude reaction product of the hydrogenolysis reactor 152 comprises at least 5% more ethanol than the gaseous portion of the second distillate in via 138, e.g., at least 10% more ethanol, or at least 25% more ethanol. Other components, such as water, acetaldehyde, and other impurities may be present in the crude product of the hydrogenolysis reactor 152 in minor amounts.

The crude reaction product in line 156, which may be referred to as a second crude ethanol product, may be condensed and fed to separator 153, which, in turn, provides a vapor stream and a liquid stream. The separator 153, e.g., a flasher or knock-out pot, in one embodiment operates at a temperature of from 50° C. to 500° C., e.g., from 70° C. to 400° C. or from 100° C. to 350° C. In one embodiment, the pressure of separator 106 is from 50 kPa to 2000 kPa, e.g., from 75 kPa to 1500 kPa, or from 100 kPa to 1000 kPa.

The vapor stream exiting the separator 153 may comprise hydrogen and hydrocarbons, which may be purged and/or returned to reaction zone 101 via line 155. As shown in FIG. 1A, the returned portion of the vapor stream in line 155 is combined with the hydrogen vapor stream of line 113 that passes through compressor 114.

The liquid stream exiting the separator 153 comprises ethanol and is preferably returned to the separation zone 102 via line 157. As shown in FIG. 1A, the liquid stream in line 157 is returned to the second column 108. Additionally or alternatively, a portion of the liquid stream in line 157 may be fed to the third column 109. In other embodiments, all or a portion of the liquid stream in line 157 may be returned to any of the other columns in the separation zone 102, such as column 107, or to the reaction zone 101, e.g., to the reactor 103.

FIG. 1B shows an embodiment in which a liquid portion of the second distillate 120 is directed via line 139 to the hydrogenolysis zone 150. The liquid portion in line 139 is fed to a vaporizer 154 along with hydrogen feed stream 104. Vaporizer 154 generates a vapor feed stream in line 140 that is fed to the hydrogenolysis reactor 152. The hydrogenolysis reaction is carried out in a similar manner as described above for FIG. 1A. The crude reaction product is preferably sent to the separator 153 via line 156. The crude reaction product is separated in the separator 153 into a vapor stream and a liquid stream, and the liquid stream is preferably introduced to the second column via line 157.

Although the second distillate may be introduced to the hydrogenolysis reactor 152, in some embodiments the first distillate may also be introduced to the hydrogenolysis reactor 152. The first distillate may be introduced independently of the second distillate or may be combined with a portion of the second distillate. In addition, the first and second distillate may be combined with all or a portion of the fourth residue, as described below, and fed to the hydrogenolysis zone 150.

In another embodiment, shown in FIG. 2, the second distillate is fed via line 120 to fourth column 123, also referred to as the "acetaldehyde removal column." In fourth column 123, the second distillate in line 120 is separated into a fourth distillate, which comprises acetaldehyde, in line 124 and a fourth residue, which comprises ethyl acetate, in line 125. The fourth distillate preferably is refluxed at a reflux ratio of from 1:20 to 20:1, e.g., from 1:15 to 15:1 or from 1:10 to 10:1, and a portion of the fourth distillate is directly or indirectly returned to the reaction zone 101 as shown by line 124. For example, the fourth distillate may be combined with the acetic acid feed, added to the vaporizer 110, or added directly to the reactor 103. As shown, the fourth distillate is co-fed with the acetic acid in feed line 105 to vaporizer 110. Without being bound by theory, since acetaldehyde may be hydrogenated to form ethanol, the recycling of a stream that contains acetaldehyde to the reaction zone increases the yield of ethanol and decreases byproduct and waste generation. In another embodiment (not shown), the acetaldehyde may be collected and utilized, with or without further purification, to make useful products including but not limited to n-butanol, 1,3-butanediol, and/or crotonaldehyde and derivatives.

In one embodiment, a liquid portion or all of the fourth residue in line 125, is directed via line 141 to a vaporizer 154 along with hydrogen feed stream 104. A portion of the fourth residue of fourth column 123 may also be purged from line 125. Vaporizer 154 generates a vapor feed stream in line 140 that is fed to the hydrogenolysis reactor 152. The hydrogenolysis reaction is carried out in a similar manner as described above for FIGS. 1A and 1B. The crude reaction product is preferably sent to the separator 153 via line 156. The crude reaction product is separated in the separator 153 into a vapor stream and a liquid stream, and the liquid stream is preferably introduced to the second column via line 157. Vapor stream 155 exiting the separator 153 may comprise hydrogen and hydrocarbons, which may be purged and/or returned to reaction zone 101 via line 155. As shown in FIG. 2, the returned portion of the vapor stream in line 155 is combined with the hydrogen vapor stream of line 113 that passes through compressor 114.

Fourth column 123 is preferably a tray column as described above and preferably operates above atmospheric pressure. In one embodiment, the operating pressure is from 120 kPa to 5,000 kPa, e.g., from 200 kPa to 4,500 kPa, or from 500 kPa to 3,000 kPa. In a preferred embodiment, the fourth column 123 may operate at a pressure that is higher than the pressure of the other columns.

The temperature of the fourth distillate exiting in line 124 from fourth column 123 preferably is from 60° C. to 110° C., e.g., from 70° C. to 100° C. or from 75° C. to 95° C. The temperature of the residue exiting from fourth column 125 preferably is from 70° C. to 115° C., e.g., from 80° C. to 110° C. or from 85° C. to 110° C. Exemplary components of the distillate and residue compositions for fourth column 109 are provided in Table 6. It should be understood that the distillate and residue may also contain other components, not listed, such as components in the feed.

TABLE 6

| FOURTH COLUMN | | | |
|---|---|---|---|
| | Conc. (wt. %) | Conc. (wt. %) | Conc. (wt. %) |
| Distillate | | | |
| Acetaldehyde | 2 to 80 | 2 to 50 | 5 to 40 |
| Ethyl Acetate | <90 | 30 to 80 | 40 to 75 |
| Ethanol | <30 | 0.001 to 25 | 0.01 to 20 |
| Water | <25 | 0.001 to 20 | 0.01 to 15 |
| Residue | | | |
| Ethyl Acetate | 40 to 100 | 50 to 100 | 60 to 100 |
| Ethanol | <40 | 0.001 to 30 | 0 to 15 |
| Water | <25 | 0.001 to 20 | 2 to 15 |
| Acetaldehyde | <1 | 0.001 to 0.5 | Not detectable |
| Acetal | <3 | 0.001 to 2 | 0.01 to 1 |

Figure 3:
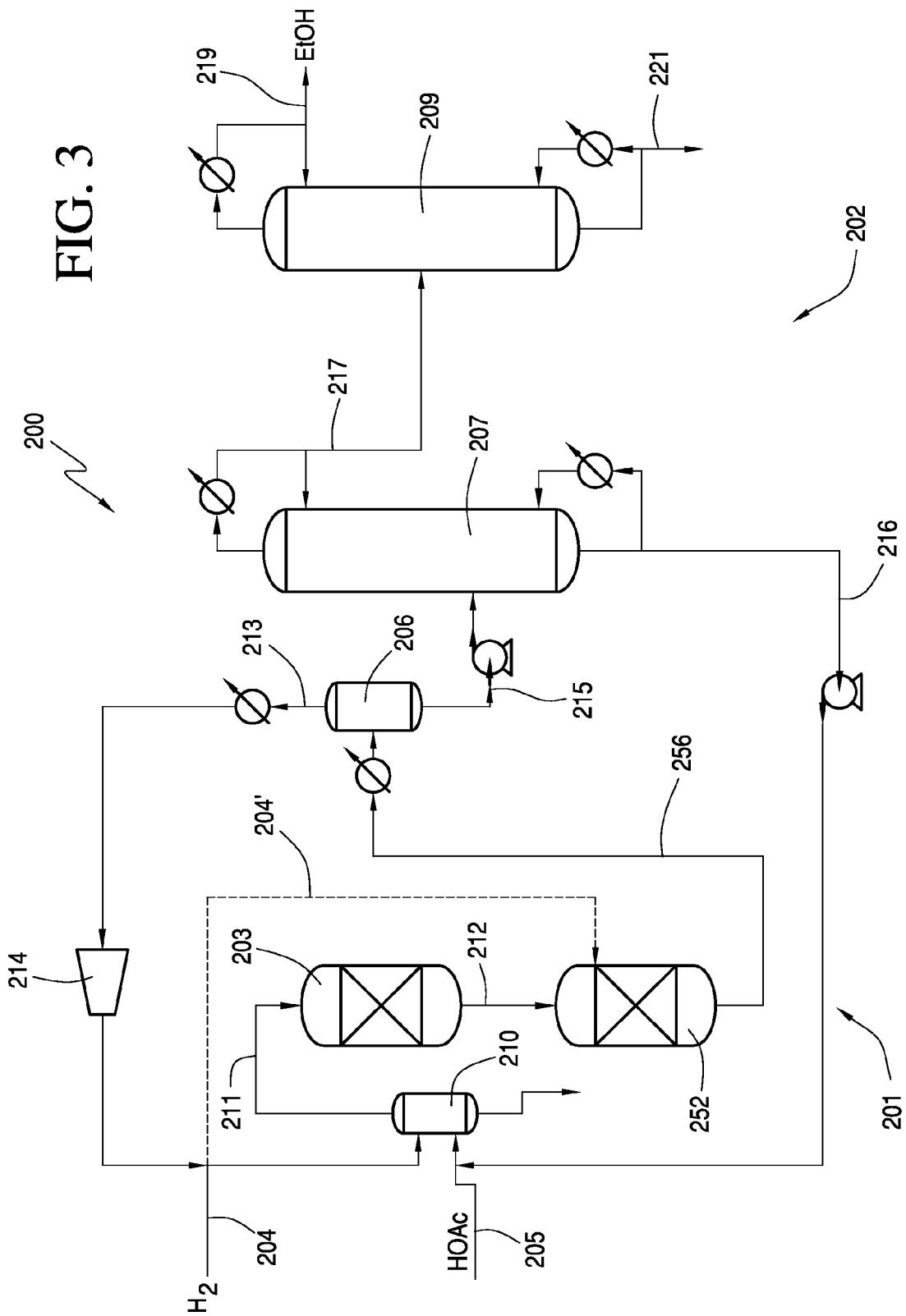
FIG. 3 is a schematic diagram of a reaction zone comprising a hydrogenation and hydrogenolysis reactor in accordance with one embodiment of the present invention.

FIG. 3 shows another embodiment of the present invention of a hydrogenation system 200. System 200 comprises reaction zone 201 and separation zone 202. Reaction zone 201 comprises hydrogenation reactor 203, hydrogen feed stream 204, acetic acid feed stream 205, hydrogenolysis reactor 252, and vaporizer 210. separation zone 202 comprises separator 206, acid separation column 207, referred to above as the first column, and product column 209, referred to above as the third column. Preferably, the system 200 shown in FIG. 3 does not have a light ends column and/or an aldehyde removal column. Reducing distillation columns in system 200 may advantageously improve the efficiency to recover ethanol with less energy and capital investment. In providing a hydrogenolysis reactor 252 before the separation zone 202, the system 200 substantially reduces any ethyl acetate formed in hydrogenation reactor 203. This reduces the separation processing necessary to remove ethyl acetate from the crude ethanol product.

Hydrogen and acetic acid may be separately fed or jointly fed to a vaporizer 210 from feed streams 204 and 205. Vaporizer 210 generates a vapor feed stream in line 211 that is directed to reactor 203. The temperature of the vapor feed stream in line 211 is preferably from 100° C. to 350° C., e.g., from 120° C. to 310° C. or from 150° C. to 300° C. Any feed that is not vaporized is removed from vaporizer 210, as shown, and may be recycled thereto. Vapor feed stream in line 211 is first fed to reactor 203 to hydrogenate the acetic acid, preferably in the presence of a catalyst.

During the hydrogenation process, a crude ethanol product stream is withdrawn, preferably continuously, from reactor 203 via line 212. The crude ethanol product stream, which comprises ethyl acetate in addition to ethanol and water, may be fed to the hydrogenolysis reactor 252 for the formation of additional ethanol from the ethyl acetate. In one aspect, the crude ethanol product includes residual hydrogen in an amount sufficient to perform the hydrogenolysis reaction on the ethyl acetate in hydrogenolysis reactor 252. In another aspect, additional hydrogen from feed stream 204' is fed to hydrogenolysis reactor 252. In some embodiments, the crude ethanol product stream may be preheated before being fed to hydrogenolysis reactor 252.

A crude product stream 256 may be continuously withdrawn from hydrogenolysis reactor 252, condensed and fed to separator 206, e.g., a flasher or knock-out pot. Separator 206, in turn, provides a vapor stream and a liquid stream. The separator 206, in one embodiment, operates at a temperature of from 50° C. to 500° C., e.g., from 70° C. to 400° C. or from 100° C. to 350° C. In one embodiment, the pressure of separator 206 is from 50 kPa to 2000 kPa, e.g., from 75 kPa to 1500 kPa, or from 100 kPa to 1000 kPa.

The vapor stream exiting the separator 206 may comprise hydrogen and hydrocarbons, which may be purged and/or returned to reaction zone 201 via line 213. As shown, the returned portion of the vapor stream passes through compressor 214 and is combined with the hydrogen feed stream 204 and is fed to vaporizer 210. The returned portion of the vapor stream in line 213 may also be combined with the feed stream 204' and is fed to the hydrogenolysis reactor 252.

The liquid from separator 206 is withdrawn and pumped via line 215 to the side of acid separation column 207, as described above. The liquid in line 215 preferably has a reduced ethyl acetate concentration, e.g., at least 5% less ethyl acetate than the crude ethanol product in line 212, at least 75% less ethyl acetate, or at least 90% less ethyl acetate. The other components of liquid in line 215 are described in Table 2. The residue from the acid separation column 207 in line 216 may be returned to the reaction zone 201. The distillate from the acid separation column 207 in line 217 preferably is directly fed to the product column 209. The distillate from the acid separation column 207 in line 217 preferably has a reduced amount of ethyl acetate. The other components of liquid in line 215 are described in Table 3. Acid separation column 207 and product column 209 operate in similar manner as described above in FIGS. 1A, 1B, and 2. Ethanol may be obtained from the distillate of product column 209 in stream 219. The residue of product column 209 in line 221 comprises water and preferably is purged from system 200.

Figure 4A:
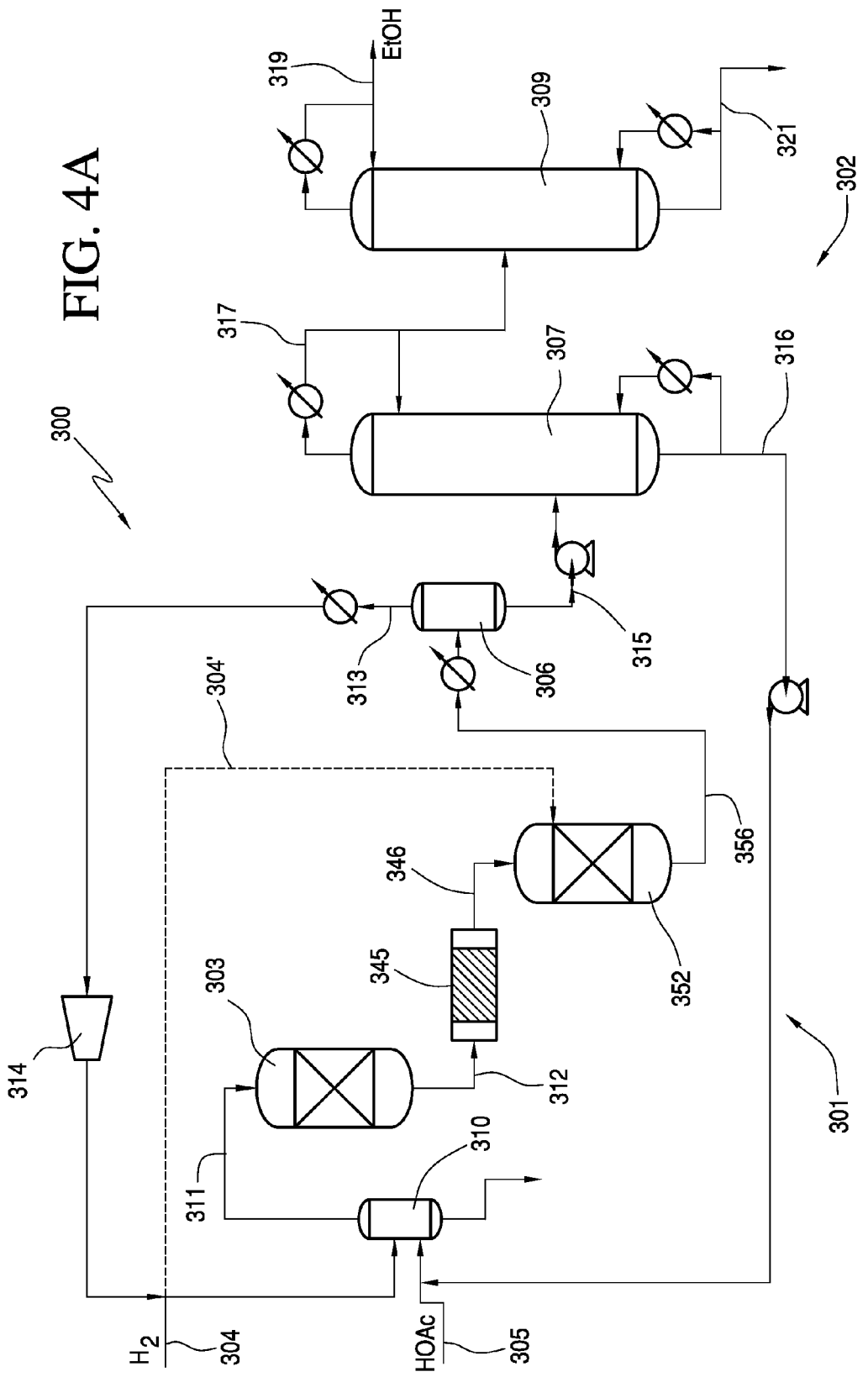
FIG. 4A is a schematic diagram of a reaction zone comprising a hydrogenation, esterification, and hydrogenolysis reactor in accordance with one embodiment of the present invention.
Figure 4B:
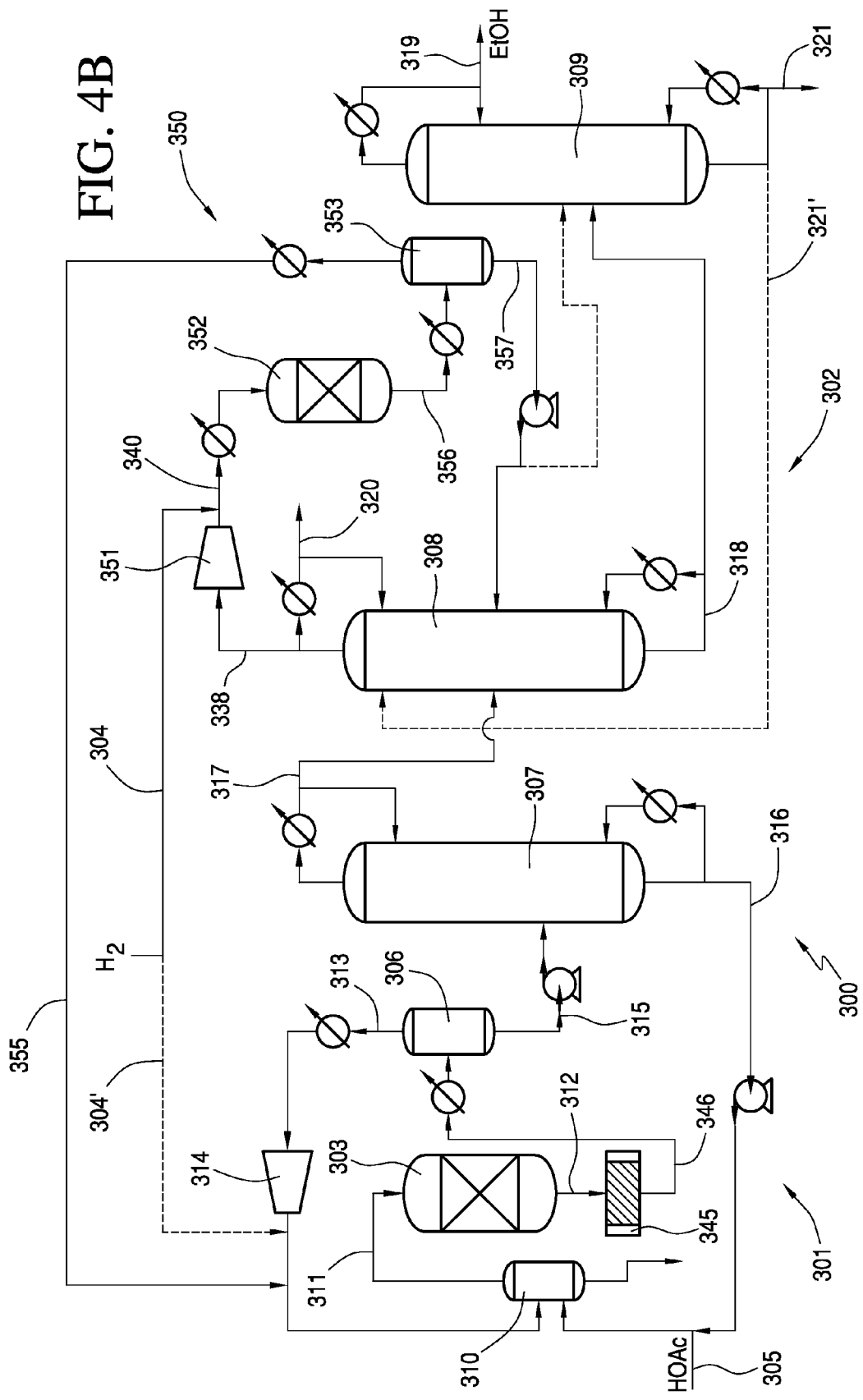
FIG. 4B is a schematic diagram of a reaction zone comprising a hydrogenation, and esterification reactor and a derivative stream thereof is directed to a hydrogenolysis reactor in accordance with one embodiment of the present invention.

In FIGS. 4A and 4B another hydrogenation system 300 is shown that comprises an esterification reactor 345 according to one embodiment of the present invention. The esterification reactor 345 produces additional ethyl acetate by esterifying residual acetic acid and ethanol in the crude ethanol product. This approach advantageously reduces or eliminates acetic acid from the crude ethanol product thereby simplifying the separation process since it is unnecessary to include a step of removing acetic acid from the crude ethanol product. The subsequent hydrogenolysis of thus produced ethyl acetate forms additional ethanol.

In FIG. 4A, system 300 comprises a reaction zone 301 and a separation zone 302. Reaction zone 301 comprises hydrogenation reactor 303, hydrogen feed stream 304, acetic acid feed stream 305, esterification reactor 345, hydrogenolysis reactor 352, and vaporizer 310. Separation zone 302 comprises separator 306, e.g., a flasher or knock-out pot, acid separation column 307, referred to above as the first column, and product column 309, referred to above as the third column. The system 300 in FIG. 4A is similar to the one shown in FIG. 3, with the addition of an esterification reactor 345.

Hydrogen and acetic acid may be separately fed or jointly fed to a vaporizer 310 from feed streams 304 and 305. Vaporizer 310 generates a vapor feed stream in line 311 that is directed to hydrogenation reactor 303. A crude ethanol product stream may be continuously withdrawn from reactor 303 via line 312 and fed to esterification reactor 345. In some embodiments, the crude ethanol product stream may be cooled before being fed to esterification reactor 345.

An esterification reaction product in line 346 may be continuously withdrawn and fed to hydrogenolysis reactor 352. In one embodiment, the esterification reaction product in line 346 includes sufficient residual hydrogen to perform the hydrogenolysis reaction in reactor 352. Alternatively, additional hydrogen from feed stream 304' may be fed to hydrogenolysis reactor 352. In some embodiments, the esterification reaction product 346 may be preheated before being fed to hydrogenolysis reactor 352. A crude product stream 356 may be continuously withdrawn from hydrogenolysis reactor 352, condensed and fed to separator 306. Separator 306, operating at conditions described above, in turn, provides a vapor stream and a liquid stream. The vapor stream exiting the separator 306 may comprise hydrogen and hydrocarbons, which may be purged and/or returned to reaction zone 301 via line 313. As shown, the returned portion of the vapor stream passes through compressor 314 and is combined with the hydrogen feed stream 304 and fed to vaporizer 310. The returned portion of the vapor stream in line 313 may also be combined with the feed stream 304' and fed to the hydrogenolysis reactor 352.

The liquid from separator 306 is withdrawn and pumped via line 315 to the side of acid separation column 307, as described above. The liquid in line 315 in FIG. 4A preferably has a reduced ethyl acetate concentration. The other components of liquid in line 315 are described in Table 2. The residue from the acid separation column 307 in line 316 may be returned to the reaction zone 301. The distillate from the acid separation column 307 in line 317 preferably is directly fed to the product column 309. The distillate from the acid separation column 307 in line 317 preferably has a reduced amount of ethyl acetate. The other components of liquid in line 315 are described in Table 3. Acid separation column 307 and product column 309 operate in similar manner as described above. Ethanol may be obtained from the distillate of product column 309 in stream 319. The residue of product column 309 in line 321 comprises water and preferably is purged from system 300.

In one optional embodiment, the liquid stream 315 comprises a reduced amount of acetic acid, due to the consumption of the acetic acid in the esterification reaction, and liquid stream 315 may be directly fed to product column 309 without being separated in acid separation column 307.

In FIG. 4B, system 300 comprises reaction zone 301, separation zone 302, and hydrogenolysis zone 350. Reaction zone 301 comprises hydrogenation reactor 303, acetic acid feed stream 305, esterification reactor 345, and vaporizer 310. Separation zone 302 comprises a separator 306, e.g., flasher or knock-out pot, acid separation column 307, light ends column 308, referred to as the second column above, and product column 309. Hydrogenolysis zone 350 comprises hydrogen feed stream 304 and hydrogenolysis reactor 352. The system 300 in FIG. 4A is similar to the one shown in FIG. 1A, with the addition of an esterification reactor 345. In other embodiments, the esterification reactor 345 may be combined with the features taught in FIG. 1B and/or FIG. 2.

As described above, hydrogen is preferably fed to the hydrogenolysis zone 350 and introduced to the reaction zone 301 via line 355. Optionally, hydrogen may also be fed directly to the reaction zone 301 via line 304'. Hydrogen, either fed directly from line 304', indirectly from line 355 or a combination of both, and acetic acid via line 305 may be fed to a vaporizer 310. Similar to FIG. 4A, the vaporized feed stream 311 is fed to the hydrogenation reactor 303 to produce a crude ethanol product in line 312 which is fed to the esterification reactor 345 to produce an esterification reaction product in line 346. The esterification reaction product in line 346 may be condensed and fed to a separator 306 to produce a vapor stream and liquid. The vapor stream exiting the separator 306 may comprise hydrogen and hydrocarbons, which may be purged and/or returned to reaction zone 301 via line 313. The liquid from separator 306 is withdrawn and pumped via line 315 to the side of acid separation column 307, as described above. In FIG. 4B, the liquid in line 315 preferably has an increased ethyl acetate concentration. The liquid in line 315 preferably has a reduced amount of acetic acid, which is consumed in the esterification reactor 345. The other components of liquid in line 315 are described in Table 2. The residue in line 316, depending on the water concentration, may be returned to the reactor zone 301.

The distillate from the acid separation column 307 in line 317 preferably is directly fed to the light ends column 308. The light ends column 308 produces a residue of ethanol and water that is fed to the product column 309 via line 318 and a distillate. A portion of the distillate from column 308 may be purged via line 320, and another portion of the distillate, preferably a gaseous portion in line 338, is withdrawn and fed to hydrogenolysis zone 350 as described above in FIG. 1A. The gaseous portion in line 338 may be compressed to form a stream in line 340 that is combined with the hydrogen feed stream 304. The combined stream 340 is preferably fed to the hydrogenolysis reactor 352 to produce a crude product in line 356. The crude product may be condensed and separated in separator 353 into a vapor stream in line 355 and a liquid stream in line 357. Vapor stream in line 355 may be purged and/or introduced to reaction zone 301. The liquid stream is preferably fed to the light ends column 308 via line 357 and may optionally also be fed to the product column 309 and/or acid column 307.

In one optional embodiment, the liquid stream from separator 306 comprises a reduced amount of acetic acid, as indicated above, and the liquid stream may be directly fed to light ends column 308 without being separated in acid separation column 307.

Figure 5:
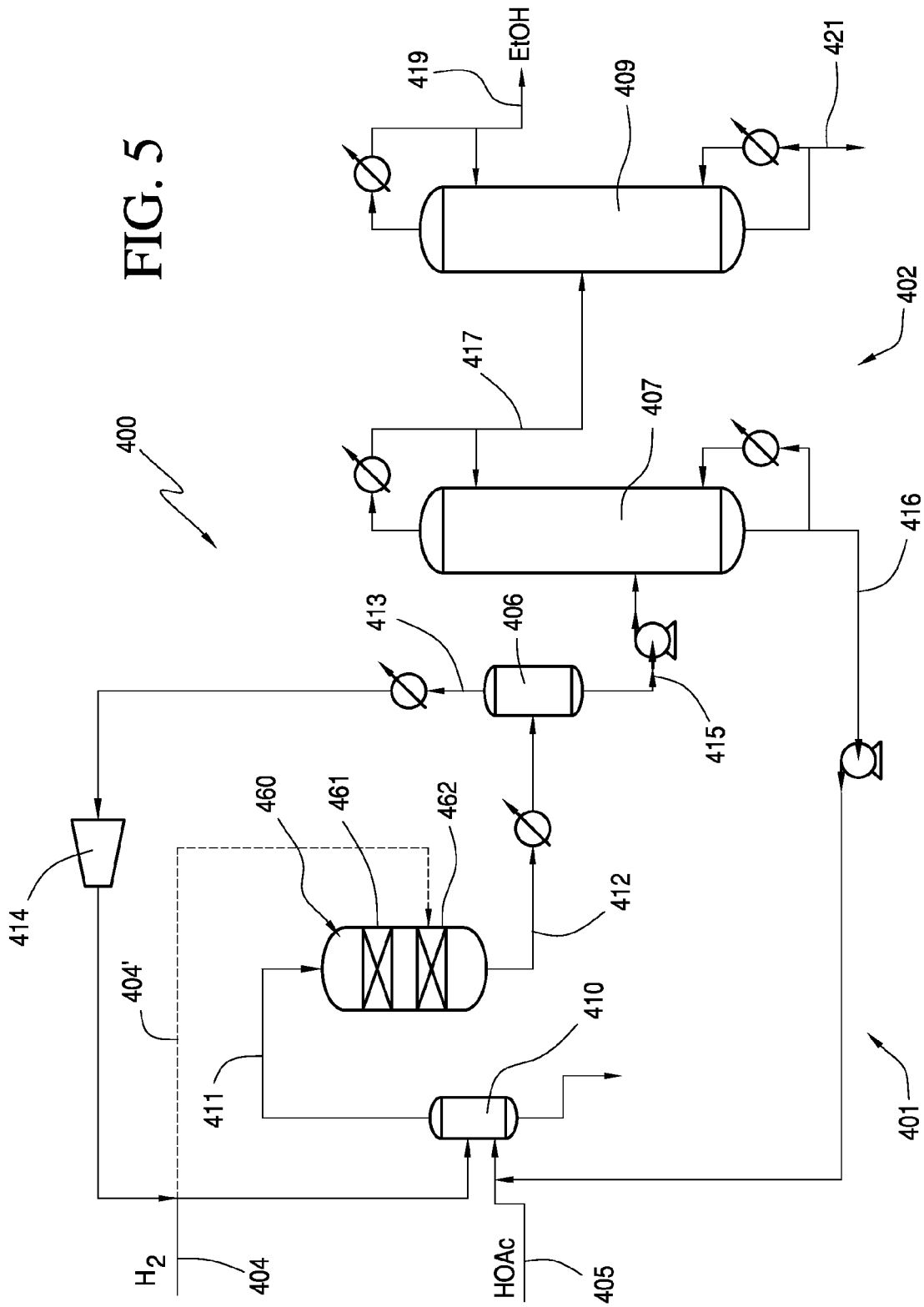
FIG. 5 is a schematic diagram of a reaction zone comprising a reactor having a hydrogenation section and hydrogenolysis section in accordance with one embodiment of the present invention.

Returning to FIG. 3, two separate reactors are shown for hydrogenation and hydrogenolysis, respectively. In some embodiments, a single reactor having both hydrogenation and hydrogenolysis catalyst contained therein or a single reactor having separate zones is employed, as shown in FIG. 5. The hydrogenation system 400 in FIG. 5 comprises reaction zone 401 and separation zone 402. Reaction zone comprises a reactor 460 having hydrogenation zone 461 and hydrogenolysis zone 462. The separation zone comprises separator 406, e.g., a flasher or knock-out pot, acid separation column 407 and/or product column 409.

Hydrogen and acetic acid may be separately fed or jointly fed to a vaporizer 410 from feed streams 404 and 405. Vaporizer 410 generates a vapor feed stream in line 411 that is directed to reactor 460. Preferably, the vapor feed stream in line 411 passes through the hydrogenation zone 461 and then through the hydrogenolysis zone 462. Although not shown, there may be multiple hydrogenation and hydrogenolysis zones, as well as optional esterification zones. A crude ethanol product stream is withdrawn, preferably continuously, from reactor 460 via line 412. The crude ethanol product may be condensed and fed to separator 406. Separator 406, operating under conditions described herein, in turn, provides a vapor stream and a liquid stream.

The vapor stream exiting the separator 406 may comprise hydrogen and hydrocarbons, which may be purged and/or returned to reaction zone 401 via line 413. As shown, the returned portion of the vapor stream passes through compressor 414 and is combined with the hydrogen feed stream 404 and fed to vaporizer 410. The returned portion of the vapor stream in line 413 may also be combined with the feed stream 404' and fed to the hydrogenolysis zone 462.

The liquid from separator 406 is withdrawn and pumped via line 415 to the side of acid separation column 407, as described above. The liquid in line 415 preferably has a reduced amount of ethyl acetate. The other components of liquid in line 415 are described in Table 2. The residue in line 416 may be returned to the reaction zone 401. The distillate in line 417 preferably is directly fed to the product column 409. Distillate in line 417 also preferably has a reduced amount of ethyl acetate. The other components of liquid in line 415 are described in Table 3. Acid separation column 407 and product column 409 operate in a similar manner as described above. Ethanol may be obtained from the distillate of product column 409 in stream 419. The residue of product column 409 in line 421 comprises water and preferably is purged from system 400.

The ethanol composition obtained by the processes of the present invention may be an industrial grade ethanol comprising from 75 to 96 wt. % ethanol, e.g., from 80 to 96 wt. % or from 85 to 96 wt. % ethanol, based on the total weight of the finished ethanol composition. Exemplary finished ethanol compositional ranges are provided below in Table 7.

TABLE 7

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be higher than indicated in Table 7, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including applications as fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

While the invention has been described in detail, modifications within the spirit and scope of the invention will be readily apparent to those of skill in the art. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing ethanol, comprising the steps of:
  hydrogenating acetic acid in a first reactor in the presence of a catalyst to form a first crude ethanol product;
  separating at least a portion of the first crude ethanol product into an ethanol product stream and a derivative stream comprising ethyl acetate;
  reacting in a second reactor at least a portion of the derivative stream in the presence of hydrogen to form a second crude ethanol product;
  flashing at least a portion of the second crude ethanol product to generate a vapor stream comprising hydrogen; and
  introducing the vapor stream to the first reactor, wherein substantially all of the hydrogen introduced to the first reactor is obtained from the vapor stream, and
  wherein all the hydrogen fed to the process is fed to the second reactor.

2. The process of claim 1, wherein the derivative stream comprises at least 5 wt. % ethyl acetate.

3. The process of claim 1, wherein the derivative stream is a vapor derivative stream.

4. The process of claim 1, wherein the derivative stream is a liquid derivative stream.

5. The process of claim 1, wherein the first crude ethanol product is separated in one or more distillation columns.

6. The process of claim 5, further comprising the step of:
  introducing the second crude ethanol product into the one or more columns.

7. The process of claim 1, wherein the second crude ethanol product comprises at least 5% more ethanol than the at least a portion of the derivative stream fed to the second reactor.

8. The process of claim 1, wherein the at least a portion of the derivative stream is reacted in the presence of a hydrogenolysis catalyst.

9. A process for producing ethanol, comprising the steps of:
  providing a first crude ethanol product comprising ethanol, acetic acid, ethyl acetate and water;
  separating at least a portion of the first crude ethanol product into an ethanol product stream and a derivative stream comprising ethyl acetate; and
  reacting at least a portion of the derivative stream in the presence of hydrogen to form a second crude ethanol product;
  flashing at least a portion of the second crude ethanol product to generate a vapor stream comprising hydrogen; and
  introducing the vapor stream to the first reactor, wherein substantially all of the hydrogen introduced to the first reactor is obtained from the vapor stream, and
  wherein all the hydrogen fed to the process is fed to the reaction.

10. The process of claim 9, wherein the derivative stream comprises at least 5 wt. % ethyl acetate.

11. The process of claim 9, wherein the derivative stream is a vapor derivative stream.

12. The process of claim 9, wherein the derivative stream is a liquid derivative stream.

13. The process of claim 9, wherein the first crude ethanol product is separated in one or more distillation columns.

14. The process of claim 13, further comprising the step of:
  introducing the second crude ethanol product into the one or more columns.

15. The process of claim 9, wherein the second crude ethanol product comprises at least 5% more ethanol than the at least a portion of the derivative stream fed to the second reactor.

16. The process of claim 9, wherein the at least a portion of the derivative stream is reacted in the presence of a hydrogenolysis catalyst.

17. A process for producing ethanol, comprising the steps of:
  hydrogenating acetic acid in a first reactor in the presence of a catalyst to form a first crude ethanol product;
  reacting in a second reactor at least a portion of the first crude ethanol product in the presence of hydrogen to form a second crude ethanol product;
  flashing at least a portion of the second crude ethanol product to generate a vapor stream comprising hydrogen; and
  introducing the vapor stream to the first reactor, wherein substantially all of the hydrogen introduced to the first reactor is obtained from the vapor stream; and
  separating at least a portion of the flashed second crude ethanol product in one or more columns to obtain ethanol;
  wherein all the hydrogen fed to the process is fed to the second reactor.

18. The process of claim 17, wherein the first crude ethanol product comprises ethyl acetate.

19. The process of claim 18, wherein the second crude ethanol product comprises less ethyl acetate than the first crude ethanol product.

20. The process of claim 17, further comprising the steps of:
esterifying the at least a portion of the first crude ethanol product to form an esterified reaction product, wherein at least a portion of the esterified reaction product is reacted in the second reactor.

21. A process for producing ethanol, comprising the steps of:
hydrogenating acetic acid in a first reactor in the presence of a catalyst to form a first crude ethanol product;
separating at least a portion of the first crude ethanol product in a first column into a first distillate comprising ethanol, water and ethyl acetate, and a first residue comprising acetic acid;
separating at least a portion of the first distillate in a second column into a second distillate comprising ethyl acetate and a second residue comprising ethanol and water;
separating at least a portion of the second residue in a third column into a third distillate comprising ethanol and a third residue comprising water;
separating at least a portion of the second distillate in a fourth column into a fourth distillate comprising acetaldehyde and a fourth residue comprising ethyl acetate; and
reacting in a second reactor at least a portion of the first distillate, at least a portion of the second distillate and/or at least a portion of the fourth residue in the presence of hydrogen to form a second crude ethanol product.

22. The process of claim 21, wherein the second distillate is a vapor derivative stream.

23. The process of claim 21, wherein the second distillate and/or the fourth residue is a liquid derivative stream.

24. The process of claim 21, further comprising the step of:
introducing the second crude ethanol product into the second column.

25. The process of claim 21, further comprising the step of:
introducing the second crude ethanol product into the third column.

26. The process of claim 21, wherein the second crude ethanol product comprises at least 5% more ethanol than the at least a portion of the first distillate, at least a portion of the second distillate and/or at least a portion of the fourth residue.

27. The process of claim 21, wherein the at least a portion of the first distillate, at least a portion of the second distillate and/or at least a portion of the fourth residue is reacted in the presence of a hydrogenolysis catalyst.

28. A process for purifying a first crude ethanol product, comprising the steps of:
providing the first crude ethanol product comprising ethanol, acetic acid, ethyl acetate and water;
separating at least a portion of the first crude ethanol product in a first column into a first distillate comprising ethanol and a first residue comprising acetic acid;
separating at least a portion of the first distillate in a second column into a second distillate comprising ethyl acetate and a second residue comprising ethanol and water;
separating at least a portion of the second residue in a third column into a third distillate comprising ethanol and a third residue comprising water;
separating at least a portion of the second distillate in a fourth column into a fourth distillate comprising acetaldehyde and a fourth residue comprising ethyl acetate; and
reacting at least a portion of the first distillate, at least a portion of the second distillate and/or at least a portion of the fourth residue in the presence of hydrogen to form a second crude ethanol product.

29. The process of claim 28, wherein the first distillate and/or the second distillate is a vapor derivative stream.

30. The process of claim 28, wherein the first distillate, the second distillate and/or fourth residue is a liquid derivative stream.

31. The process of claim 28, further comprising the step of:
introducing the second crude ethanol product into the second column.

32. The process of claim 28, further comprising the step of:
introducing the second crude ethanol product into the third column.

33. The process of claim 28, wherein the at least a portion of the first distillate, at least a portion of the second distillate and/or at least a portion of the fourth residue is reacted in the presence of a hydrogenolysis catalyst.

34. A process for hydrogenolyzing ethyl acetate, comprising:
hydrogenating acetic acid in a reactor in the presence of a catalyst to form a first crude ethanol product; and
reacting an ethyl acetate-containing stream in a hydrogenolysis unit under conditions effective to form a second crude ethanol product comprising more ethanol than the ethyl acetate-containing stream, wherein the ethyl acetate-containing stream is the first crude ethanol product or a derivative stream thereof;
flashing at least a portion of the second crude ethanol product to generate a vapor stream comprising hydrogen; and
introducing the vapor stream to the reactor, wherein substantially all of the hydrogen introduced to the first reactor is obtained from the vapor stream, and
wherein all the hydrogen fed to the process is fed to the hydrogenolysis unit.

35. The process of claim 34, wherein the second crude ethanol product comprises at least 5% more ethanol than the ethyl acetate-containing stream.

36. The process of claim 34, wherein the second crude ethanol product comprises at least 5% less ethyl acetate than the ethyl acetate-containing stream.

* * * * *